US012697201B2

(12) United States Patent
Gesché et al.

(10) Patent No.: US 12,697,201 B2
(45) Date of Patent: Aug. 4, 2026

(54) VASCULAR IMPLANT AND METHOD FOR THE PRODUCTION THEREOF

(71) Applicant: RHEINISCH-WESTFÄLISCHE TECHNISCHE HOCHSCHULE (RWTH) AACHEN, Aachen (DE)

(72) Inventors: Valentine Gesché, Aachen (DE); Alexander Löwen, Aachen (DE); Kathrin Kurtenbach, Schermbeck (DE); Thomas Gries, Aachen (DE)

(73) Assignee: RHEINISCH-WESTFÄLISCHE TECHNISCHE HOCHSCHULE, Aachen (DE)

( * ) Notice: Subject to any disclaimer, the term of this patent is extended or adjusted under 35 U.S.C. 154(b) by 963 days.

(21) Appl. No.: 17/609,360

(22) PCT Filed: May 5, 2020

(86) PCT No.: PCT/EP2020/062432
§ 371 (c)(1),
(2) Date: Nov. 5, 2021

(87) PCT Pub. No.: WO2020/225254
PCT Pub. Date: Nov. 12, 2020

(65) Prior Publication Data
US 2022/0316112 A1 Oct. 6, 2022

(30) Foreign Application Priority Data

May 6, 2019 (DE) ..................... 10 2019 206 493.0

(51) Int. Cl.
*A61F 2/07* (2013.01)
*A61F 2/04* (2013.01)
(Continued)

(52) U.S. Cl.
CPC .................. *A61F 2/07* (2013.01); *A61F 2/04* (2013.01); *A61F 2/06* (2013.01); *G06F 30/17* (2020.01);
(Continued)

(58) Field of Classification Search
CPC ........ A61F 2/06; A61F 2/07; A61F 2240/002; D10B 2509/06; D04B 37/06; D04B 21/205; G06F 30/17
See application file for complete search history.

(56) References Cited

U.S. PATENT DOCUMENTS 5,800,514 A * 9/1998 Nunez ...................... D03D 3/02
139/389
5,911,753 A 6/1999 Schmitt
(Continued)

FOREIGN PATENT DOCUMENTS

DE 10 2015 207 596 A1 10/2016
EP 1 433 440 A2 6/2004
(Continued)

OTHER PUBLICATIONS

Liberski et al., "Weaving for heart valve tissue engineering", Biotechnology Advances, 2017, pp. 633-656, vol. 35, 2017 Elsevier Inc.
(Continued)

*Primary Examiner* — Dinah Baria
(74) *Attorney, Agent, or Firm* — Benjamin A. Berkowitz; Foley & Lardner LLP

(57) ABSTRACT
The invention relates to a method for producing a vascular implant. The method comprises: obtaining vessel parameters; creating a computer-aided model of a vascular implant based on the obtained vessel parameters, wherein the vascular implant comprises one or more modules, each comprising at least one tubular liner body; selecting one or more
(Continued)

structural elements of a respective module from the group consisting of: one or more diameter changes along at least one tubular liner body, one or more bifurcations, one or more branches, one or more recesses, one or more local reinforcements, and one or more iliac vessel grafts. The method further comprises: determining parameters relating to the one or more selected structural elements; integrating the structural elements into the computer-aided model according to the determined parameters; and producing the vascular implant based on the created computer-aided model. Furthermore, the invention relates to vascular implants produced by means of the method.

21 Claims, 8 Drawing Sheets

(51) Int. Cl.

| | |
|---|---|
| *A61F 2/06* | (2013.01) |
| *D04B 37/06* | (2006.01) |
| *G06F 30/17* | (2020.01) |
| *D04B 21/20* | (2006.01) |

(52) U.S. Cl.
CPC ...... *A61F 2240/002* (2013.01); *D04B 21/205* (2013.01); *D04B 37/06* (2013.01); *D10B 2509/06* (2013.01)

(56) References Cited

U.S. PATENT DOCUMENTS

| | | | | |
|---|---|---|---|---|
| 7,244,444 | B2 * | 7/2007 | Bates | .................. A61L 31/128 |
| | | | | 424/443 |
| 2001/0056299 | A1 | 12/2001 | Thompson | |
| 2004/0193258 | A1 | 9/2004 | Ellis et al. | |
| 2006/0058638 | A1 | 3/2006 | Boese et al. | |
| 2007/0061004 | A1 | 3/2007 | Steinke et al. | |
| 2007/0293936 | A1 | 12/2007 | Dobak, III | |
| 2008/0082160 | A1 | 4/2008 | Boyden et al. | |
| 2008/0262341 | A1 * | 10/2008 | Boyden | ................. G16H 20/40 |
| | | | | 604/20 |
| 2009/0043330 | A1 | 2/2009 | To | |
| 2009/0043373 | A1 * | 2/2009 | Arnault De La Menardiere | ........ A61F 2/848 |
| | | | | 623/1.35 |
| 2011/0009948 | A1 | 1/2011 | Huang et al. | |
| 2012/0046728 | A1 * | 2/2012 | Huser | ..................... A61F 2/856 |
| | | | | 623/1.13 |
| 2012/0197382 | A1 | 8/2012 | Roeder | |
| 2013/0296998 | A1 | 11/2013 | Leotta et al. | |
| 2013/0331927 | A1 | 12/2013 | Zheng et al. | |
| 2015/0320956 | A1 | 11/2015 | Dunne | |
| 2015/0335451 | A1 | 11/2015 | Liu et al. | |
| 2017/0333133 | A1 | 11/2017 | Van Bibber et al. | |
| 2018/0245243 | A1 | 8/2018 | Krieger et al. | |
| 2019/0050507 | A1 | 2/2019 | Leotta et al. | |

FOREIGN PATENT DOCUMENTS

| | | | |
|---|---|---|---|
| EP | 1 693 009 A2 | 8/2006 | |
| EP | 2 519 190 B1 | 2/2016 | |
| GB | 2 347 861 A | 9/2000 | |
| JP | 11-511679 | 10/1999 | |
| JP | 2002-519134 | 7/2002 | |
| JP | 2004-115976 | 4/2004 | |
| WO | WO-9704152 A1 * | 2/1997 | .............. D02G 3/12 |
| WO | WO-2009/025849 A1 | 2/2009 | |
| WO | WO-2016/116748 A1 | 7/2016 | |
| WO | WO-2018/144462 A1 | 8/2018 | |

OTHER PUBLICATIONS

Zhao et al., "Study of Novel Textile Conduits for Stent-Grafts: Approaches to Improve Their Water Permeability", Advanced Materials Research, Jan. 2011, pp. 1498-1504, vols. 332-334, 2011 Trans Tech Publication Ltd., Switzerland.

International Search Report & Written Opinion of the International Searching Authority issued in International Application No. PCT/EP2020/062432, mailed Jul. 24, 2020.

Author Unkown, "Cardiovascular implants and extracorporeal systems—Vascular prostheses—Tubular vascular grafts and vascular patches", ISO 7198:2016, Switzerland (62 pages).

Denninger, "Fundamentals of Warp Knitting Code of Practice", Karl Mayer Academy, www.karlmayer.de, pp. 1-221, Obertshausen, 2008.

Erbel et al., "2014 ESC Guidelines on the diagnosis and treatment of aortic diseases", European Heart Journal, 2014, pp. 2873-2926, vol. 35, The European Society of Cardiology 2014.

Graves et al., "The Current State of Fenestrated and Branched Devices for Abdominal Aortic Aneurysm Repair", Seminars in Interventional Radiology, 2015, pp. 304-310, vol. 32, 2015 by Thieme Medical Publishers, Inc. New York NY, USA.

Lardizabal et al., "Endovascular Stent-Graft Repair of Abdominal Aortic Aneurysms", New Approaches to Aortic Diseases from Valve to Abdominal Bifurcation, Chapter 38, 2018, pp. 423-431, Elsevier Inc.

Macia et al., "Chapter 15—Preoperative Planning of Endovascular Procedures in Aortic Aneurysms", In Simone, Balocco: Computing and visualization for intravascular imaging and computer-assisted stenting, 2017, pp. 413-444, Amsterdam, Netherlands: Academic Press.

Macia et al., "Standard and fenestrated endograft sizing in EVAR planning: Description and validation of a semi-automated 3D software", Computerized Medical Imaging and Graphics, 2016, pp. 9-23, vol. 50, Elsevier Ltd.

Molinari, "Planning and Sizing with OsiriX/Horos", Chapter 4 in Koncar, Igor: Abdominal Aortic Aneurysm—From Basic Research to Clinical Practice, 2019, IntechOpen, pp. 61-82.

Oderich et al., "Sizing and Planning Fenestrated and Multibranched Endovascular Repair", In Oderich, Gustavo S.: Endovascular Aortic Repair.—2017, pp. 375-394, May Foundation for Medical Education and Research.

Resch et al., "Custom-Made Devices: Current State of the Art", Endovascular Today, Mar. 2016, pp. 90-93, vol. 15, No. 3.

Riambau et al., "FEVAR/BEVAR have limitations and do not always represent the preferred option for juxtarenal reconstruction", The Journal of cardiovascular surgery, Feb. 2020, pp. 10-17, vol. 61, No. 1, Edizioni Minerva Medica, Torino, Italy.

Simons et al., "Ten Steps—A standardized 10-step approach to the planning and sizing of a fenestrated endovascular aortic aneurysm repair", Endovascular Today Europe Supplement, Nov. 2017, pp. 8-10, vol. 16, No. 11.

Verhoeven et al., "Increasing Role of Fenestrated and Branched Endoluminal Techniques in the Thoracoabdominal Segment Including Supra- and Pararenal AAA", CardioVascular and Interventional Radiology, 2020, pp. 1779-1787, vol. 43, Springer Science Business Media, LLC.

Author Unkown, "European Standard, EN 13392", Mar. 2001, Textiles Monofilaments, Determination of linear density, English version of DIN EN 13392, 7 pages, CEN Brussels.

Author Unkown, "International Standard, ISO 2060", 1994, Second Edition, , Textiles—Yarn from packages—Determination of linear density (mass per unit length) by the skein method, 16 pages, ISO 1994, Switzerland.

* cited by examiner

100

1

2

72

32

12

30

1

2

12

30

(A)          (B)

VASCULAR IMPLANT AND METHOD FOR THE PRODUCTION THEREOF

CROSS-REFERENCE TO RELATED APPLICATIONS

The present application is a National Stage entry of International Patent Application No. PCT/EP2020/062432, filed on May 5, 2020, which claims priority to and the benefit of German Patent Application No. 10 2019 206 493.0, filed on May 6, 2019. The contents of these applications are hereby incorporated by reference in their entireties.

The present invention relates to a method for producing a vascular implant, in particular an endoluminal and/or endovascular implant, wherein the vascular implant comprises one or more modules, each having at least one tubular liner body, and wherein in particular a computer-aided model of the vascular implant is created based on obtained vessel parameters and one or more queried and/or input structural elements of a respective module are integrated into the computer-aided model.

Vessels are of great importance for the function of the human body, since they can transport and/or temporarily store fluids depending on their design. Numerous factors such as aging, nutrition, stress or disease can lead to alterations in the vessels, especially the blood vessels, over time. Alterations with respect to the elasticity and stability of the vessel walls, which often affect the diameter of the vessels, as well as, for example, alterations with respect to the function of flaps acting as valves are particularly fraught with risk.

In particular, local changes in a vessel wall are not uncommon and can be extremely critical for patients depending on the affected vessel and localization. Aneurysms are an example of a local alteration in the vessel wall, wherein different definitions of the term "aneurysm" are used. For example, vessel wall alterations resulting in an increase in the diameter of the affected vessel, generally an increase of at least 50% compared to the diameter of an intact vessel in the respective area, can be termed an aneurysm. The absolute diameter of a vessel in the area of the vessel wall alteration can also be used as an indication of an aneurysm, for example, in the case of an abdominal aorta from 5 cm to 5.5 cm in men or from 4.5 cm to 5 cm in women. Also in the case of other vessels, such as thoracic or thoracoabdominal aortas, corresponding values, possibly with a slight deviation, can be used as an indication of an aneurysm. As the case may be, the increase in the vessel diameter can also be smaller, especially when the alteration progresses comparatively rapidly. For example, an increase in the vessel diameter of at least 5 mm within 6 months can indicate an aneurysm and thus an increased risk of rupture of the affected vessel.

Vascular implants are a frequently used option for reducing the risk associated with vascular alterations, for example, by bridging or replacing the respective section of the vessel. For example, a dilated vessel (such as a vessel with an aneurysm according to one of the preceding definitions) can be bridged or replaced by a stent graft. An endovascular implant, such as a stent graft, can thus ensure blood flow in the respective vessel to a clinically safe extent and prevent rupture in the case of, for example, an aneurysm.

The aforementioned stent grafts are an example of endovascular implants. A stent graft is a hollow cylinder with longitudinal extension which has at least one tubular liner body, the graft and a stent structure for stabilization. Stent grafts can have a modular structure. For example, the graft can comprise at least one main liner body and at least one further liner body, wherein the further liner bodies can have the same or comparable or even different diameters, and the stent structure can comprise one or more stent structure elements. The stent structure and the graft are typically produced in separate production processes and subsequently assembled, for example by suturing. Examples of such vascular implants are known, for example, from GB 2 347 861 A, US 2004/193258 A1 or also U.S. Pat. No. 5,911,753 A, and available products are already routinely used.

Commercially available woven grafts exhibit different weave patterns (compare Zhao et al., 2011, Adv. Mat. Res. 332-334: 1498-1504). For example, grafts from Cook Medical, Bloomington, USA, are made from multifilament threads and exhibit a 1/1 planar weave pattern, also referred to as plain weave. In contrast, grafts from Vascutek Limited, a Terumo company, Inchinnan, Scotland, United Kingdom, are made from monofilament threads and exhibit a 4/4 twill weave pattern.

As regards the individual vascular geometry of each patient, patient-individualized solutions are desirable, if not even necessary, in addition to clinically established standard products. However, such patient-individualized solutions are still associated with comparatively high sales prices and many as well as time-consuming production steps. Patient-specific medical image data such as data from CT procedures can already be three-dimensionally displayed and processed using commercially available computer programs, for example with programs such as Aquarius iNtuition EVAR (Vessel Analysis) Planning from TeraRecon, Inc., Foster City, California, USA, or also the program 3mensio Vascular from Pie Medical Imaging BV, Maastricht, the Netherlands. However, such computer programs provide no or no efficient translation of the image data into formats that can be used by machines for producing vascular implants, in particular not textile and/or textile-based vascular implants such as grafts. In addition, there is a lack of respectively required interfaces for data transfer.

A method for creating an individualized stent graft based on a digital 3D model is known, for example, from DE 10 2015 207 596 A1. In this method, however, a plurality of plastic or synthetic resin layers are applied onto one another by means of an additive process. However, it seems doubtful that the diverse clinical requirements for such an endovascular support can be met in this way.

A further method for producing an individualized vascular implant is known from US 2019/0050507 A. In this method, a model of a vessel is generated, on the basis of which a standard vascular implant is modified.

Against this background, the present invention intends to provide an automatable, time- and cost-efficient method that simplifies the production of individualized vascular implants, in particular individualized endovascular implants. Furthermore, the invention intends that the produced vascular implants have a high biocompatibility and meet the requirements in clinical practice. This includes, in particular, the consideration of patient-specific anatomical features in the respective section of the respective vessel to be supported and/or bridged by the implant.

According to the invention, this is achieved by a method and a vascular implant, in particular an endovascular implant, according to the independent claims, wherein advantageous embodiments with expedient further modifications of the invention are indicated in the respective dependent claims. Advantageous embodiments of one aspect of the invention are to be regarded as mutually advantageous embodiments of the respective other aspect of the invention.

A first aspect of the invention relates to a method for producing a vascular implant, in particular an endovascular implant, comprising the following steps: obtaining vessel parameters; creating a computer-aided model of a vascular implant based on the obtained vessel parameters, wherein the vascular implant comprises one or more modules, each comprising at least one tubular liner body; selecting one or more structural elements of a respective module from the group consisting of: one or more diameter changes along at least one tubular liner body, one or more bifurcations, one or more branches, one or more recesses, one or more local reinforcements; determining parameters relating to the one or more selected structural elements; integrating the structural elements into the computer-aided model according to the determined parameters; and producing the vascular implant on the basis of the created computer-aided model. The vascular implant is textile and/or textile-based, preferably a woven fabric and/or a knitted fabric. In particular, the vascular implant can be produced using the jacquard technique. "Selecting" a structural element, means manually, semi-automatically or fully automatically selecting it. A manual or semi-automatic selection can comprise a query for input of the desired structural element or elements by a user. Producing the vascular implant on the basis of the created computer-aided model comprises in particular warp knitting the vascular implant on the basis of said model, in particular warp knitting using the jacquard technique.

The method according to the invention for manufacturing a vascular implant, in particular an endovascular implant, comprising one or more modules each having at least one tubular liner body, thus comprises in particular the creation of a computer-aided model of the vascular implant based on respectively obtained patient-specific vessel parameters, wherein one or more structural elements are integrated into said computer-aided model upon a respective query and wherein said model is then used for producing the textile and/or textile-based vascular implant.

In the context of the present invention, the term "vascular implant" refers to an implant or also a prosthesis that can be inserted into a vessel, in particular a blood vessel, in order to bridge or also replace a respective vessel section. The vascular implant can also be used for an anastomosis to a (diseased or otherwise also healthy) vessel, in particular to a (diseased or healthy) blood vessel. In this connection, a vascular implant according to the invention comprises one or more modules each having at least one tubular liner body. A vascular implant according to the invention, for example an endovascular implant according to the invention, can further be configured to be inserted in an individual vessel or to extend in more than one vessel. The latter is advantageous, for example, when the section to be replaced or bridged is located at or near a branching of the vessel. The term "vascular implant" as used hereinafter is to be understood synonymously, unless otherwise indicated.

In the context of the present invention, the term "vessel" refers to any type of hollow tubular body, in particular of the human body, capable of transporting and/or storing at least one fluid such as, for example, a gas and/or a liquid. The term does not exclusively, but particularly, refer to hollow vessels such as blood vessels. The vessel can be located in different regions of the body, for example in the extremities or in the brain, but in particular in the abdomen and/or thorax.

In the following, "a vessel section to be bridged", "a vessel section to be replaced" or also "a vessel section for which a vascular implant, such as an endovascular implant, is to be produced" refers in particular to a section of a vessel with a genetically caused and/or acquired vessel wall alteration which is to be lined, bridged and/or replaced. The expressions are to be understood synonymously and refer to the locally limited section of the respective vessel with the vessel wall alteration as well as to the sections directly adjacent thereto. For clarification, the latter can also be additionally indicated, for example as "the vessel section to be replaced and the vessel sections directly adjacent thereto" or in the form of comparable expressions. Furthermore, the vascular implant can also be inserted in vessels or vessel areas in which there is no vessel wall alteration or weakening, for example when an anastomosis is to be produced in a healthy vessel wall area.

In the context of the present invention, the term "vessel parameters" refers to conditions, geometry and/or properties that a vessel in the respective section to be bridged and/or replaced (i) exhibits, (ii) would exhibit if there were no vessel wall alteration taking into account various factors, such as age, gender and/or body weight, and/or (iii) exhibited before a respective vessel wall alteration occurred. The term can refer to the section of the vessel exhibiting the vessel wall alteration and/or can also include conditions, geometry and/or properties of the directly adjacent vessel sections. Vessel parameters can include geometric parameters and optionally also morphological parameters. Geometric parameters can be, for example, parameters relating to vessel courses, diameters, shapes of the cross-section and/or alterations thereto, lengths, angles and/or positions of the respective vessel section, such as a vessel section to be replaced. Morphological parameters can be, for example, parameters relating to the presence of calcification and/or thrombi and/or indicating the degree of calcification, the amount of thrombi and/or the extension of the area affected by a respective degree of calcification and/or amount of thrombi in the respective vessel section to be replaced and/or in vessel sections directly adjacent thereto.

According to the method of the invention, firstly vessel parameters with respect to the respective vessel section to be bridged are obtained. They relate in particular to conditions, geometry and/or properties exhibited by a vessel in the section to be bridged and/or replaced. The obtained vessel parameters preferably comprise patient-specific information regarding diameter, diameter changes and/or length of the vessel section to be replaced. Alternatively or additionally, the vessel parameters can comprise information regarding branchings in the vessel section to be replaced, in particular regarding bifurcations and/or branches. In the context of the present application, a "bifurcation" is meant to be the splitting of the vessel into two vessels having similar diameters (such as the bifurcation of the aorta into the two iliac arteries). In the context of the present application, a "branch" is meant to be one or more smaller-diameter collateral vessels branching from a main vessel, such as the renal arteries branching off from the aorta, the outlets in the region of the aortic arch or the coronary vessels. By obtaining patient-specific vessel parameters, an optimal fit of the vascular implant to be produced for the vessel section to be replaced can be ensured and the risk of an inadequate, for example incomplete, bridging and/or replacement of the respective vessel section can be minimized. Further details on the obtained vessel parameters can be deduced from the following description of the steps relating to obtaining and visualizing image data of a vessel, identifying the vessel section for which a vascular implant (e.g., an endovascular implant) is to be produced and measuring respective vessel parameters. The vessel section can be in particular a section with an aneurysm.

The vessel parameters can be obtained on the basis of a data set of at least the vessel section to be replaced as well as the vessel sections directly adjacent thereto, said data set being obtained by an imaging method. Preparing such a data set and obtaining respective vessel parameters, for example by measuring, comprise steps known to the person skilled in the art and as implemented for example in 3mensio Vascular or comparable computer programs. The vessel parameters or corresponding data obtained by means of an imaging method can be read out from a storage medium (for example from a hard disk) or electronically transmitted as part of the method. Preferably, the obtained vessel parameters are obtained in a format readable by a respective computer program and used to create a computer-aided model of a vascular implant. Preferably, an error message is provided to the user when the vessel parameters are not obtained in a format readable by the respective computer program and/or are incomplete, for example due to a transmission error.

According to the method of the invention, a computer-aided model of a vascular implant comprising a tubular liner body is created on the basis of the obtained vessel parameters, preferably by means of a computer program. The computer-aided model can be, for example, a digital 3D model. The computer-aided model can also be only temporarily a digital 3D model that is converted into other models and/or converted from other models into a digital 3D model. For example, a digital 3D model of a vascular implant (e.g., an endovascular implant) can be used to create a 2D technical drawing. This is preferably done by the same computer program that was used to create the 3D model, but can also be done by a further computer program. A 2D technical drawing represents a geometric model of the vascular implant (e.g., the endovascular implant) that can be translated into production information for a respective production machine, preferably into a machine-readable file, in particular a KMO file. Alternatively, a KMO file can be created directly from the computer-aided 3D model. The advantage of a KMO file is that it can be read directly into a respective textile machine and the information contained in the file can be converted, in particular by means of a warp knitting machine.

A KMO file, or a comparable file, can be derived, for example, from the created 3D model (e.g., directly) or can be created from a pixel file containing the position of each needle in the respective stitch forming process, in particular a JC file. A JC file, in turn, can be derived directly from the created 3D model or can be created from a design file, such as a color-coded 2D pixel file. For example, based on the data and/or parameters provided in the form of a 3D model or a technical drawing, a color-coded 2D pixel file can be created, wherein the colors of the pixels encode respective needle positions required to produce the vascular implant. On the basis of a respective color-coded 2D pixel file, for example, in combination with information on the lapping (bar movement in the warp knitting process)—which is obtained, for example, in the form of a lapping file containing the lapping and thus the resulting stitch construction for respective guide bars—a respective predominantly used stitch construction as well as modifications thereto, such as, for example, respective stitch constructions for incorporating recesses, local reinforcements and/or separating threads, can be determined. The color-coded 2D pixel file can be converted into a JC file, wherein each color in the color-coded 2D pixel file represents a sequence of, for example, eight, preferably binary, machine instructions. In this context, the JC file is preferably a 2D pixel file which encodes various needle positions (e.g., "high" and "low") in, preferably binary encoded, pixels. A JC file can thus comprise, for example, red and white pixels. A JC file can in turn be converted into a file readable by a warp knitting machine and containing information as to the production of a respective vascular implant, in particular as to needle positions and thus as to the lapping, preferably into a KMO file. The respective digital 3D model, the respective technical drawing and/or the respective file, such as a design file, JC file and/or KMO file, is preferably stored or at least buffered, for example on a storage medium. The creation of a color-coded 2D pixel file, the transfer of respective information into a JC file and the creation of a KMO file from a respective JC file can be performed, for example, by means of a computer program, such as DesignScope Jacquard Raschel, EAT GmbH, Krefeld, Germany.

In the context of the present invention, the term "computer-aided model" thus comprises one or more digital 2D models, one or more digital 3D models, one or more technical drawings, one or more design files, one or more JC files and one or more KMO files. Preferably, the computer-aided model comprises a 3D model and/or a machine-readable file, in particular a KMO file, wherein the step of producing the vascular implant is preferably performed on the basis of the machine-readable file. This has the advantage that the parameters required for producing the vascular implant are available in a format that can be directly read and processed by machines for producing in particular textile and/or textile-based vascular implants.

The method according to the invention can further comprise a step of visualizing the computer-aided model of the vascular implant. Visualization of the model enables a visual inspection and can thereby facilitate and/or accelerate the inspection of the method during the production process. Thus, for example, missing and/or incomplete data sets can be identified at an early stage and the creation of an incomplete and/or defective vascular implant can be prevented. When, for example, the vessel parameters obtained cover only part of the vessel section to be replaced or bridged and/or of the directly adjacent vessel sections, the method according to the invention can provide for an output of a respective indication to the user. Preferably, after a respective visualization, a query is made as to whether the user agrees to proceed with the method according to the invention after a visual inspection. Furthermore, a visualization of the model enables a simulation of the implant and/or of its implantation in the vessel section. Alternatively or additionally, a simulation of the behavior of the vascular implant under mechanical stress, for example during and/or after an implantation, can be provided thereby. Furthermore, on the basis of the visual inspection and/or simulation of the vascular implant, changes can be made to one or more parameters of the computer-aided model, for example to one or more geometric parameters such as the diameter and/or length of one or more sections and/or angles between sections.

The method according to the invention further comprises the steps of selecting one or more structural elements of a respective module, determining parameters relating to the one or more selected structural elements, and integrating the structural elements into the computer-aided model according to the determined parameters. This has the advantage that the vascular implant can be optimally adapted to the respective vessel to be replaced, and can be designed according to the respective patient-specific and position-specific stresses.

This has a positive effect on the durability and functionality of the vascular implant. Depending on the configuration of the method, the query can be performed manually or automatically. The parameters can be determined by a user and/or automatically generated from the obtained vessel parameters.

The at least one structural element is selected from the group consisting of: one or more diameter changes along at least one tubular liner body, one or more bifurcations, one or more branches, one or more recesses, one or more local reinforcements and one or more iliac vessel grafts. Preferably, the at least one structural element is designed in a patient-specific manner and integrated into the respective computer-aided model of the vascular implant. In this way, an optimal fit of the vascular implant can be ensured with respect to the vessel section to be replaced or bridged and optionally the vessel sections directly adjacent thereto. This has a positive effect on the functionality and durability of the vascular implant, in particular fatigue strength, after its insertion into the respective vessel section to be bridged. Depending on the requirements resulting from the shape of the vessel, the vascular implant can comprise at least two of said structural elements, such as at least one bifurcation and one or more branches, at least one bifurcation and one or more recesses (optionally comprising one or more local reinforcements at these recesses), at least one diameter change and one or more branches, at least one diameter change and one or more recesses (optionally comprising one or more local reinforcements at these recesses), etc.

A diameter change along at least one tubular liner body of a respective module can be advantageous, particularly in relatively large vascular implants, with respect to optimal positioning and maximum functionality. For example, so-called oversizing can be advantageous, in particular in areas which are directly adjacent to the locally limited section of a respective vessel exhibiting a vessel wall alteration and which represent the area of contact between the vascular implant and the vessel wall. In the case of oversizing, the vascular implant can have a diameter that is, for example, 10% to 20% larger than that of the vessel in the respective area of contact between the vascular implant and the vessel wall. Due to oversizing, a defined radial force can act from the vascular implant on the vessel wall in the respective area of contact between the vascular implant and the vessel wall, whereby sealing and positioning the vascular implant in a positionally stable manner in the vessel section to be bridged can be ensured.

Furthermore, at least one diameter change along a respective tubular liner body can be advantageous when the respective vessel section to be replaced comprises at least one diameter change in the direction of flow of the fluid. If the diameter of the vascular implant were adapted to the smallest diameter of the vessel section to be replaced, sealing and positioning the vascular implant in a positionally stable manner in respective areas with larger diameters directly adjacent to the area of the vessel section to be replaced could be impaired. Moreover, either the fluid to be transported or stored could accumulate and/or swirl in the interstitial space or spaces formed between the vessel wall and the vascular implant, thus causing locally increased pressure onto the vessel wall. If, on the other hand, the diameter of the vascular implant were adapted to the largest diameter of the vessel section to be replaced and this were not done in the context of oversizing, this could cause locally increased pressure onto the vessel wall, which could have a detrimental effect, in areas in which the respective vessel has a smaller diameter than the vascular implant to be inserted. If the diameter of the vascular implant were adapted to the largest diameter of the vessel section to be replaced, alternatively or additionally the problem could arise that the implant cannot be optimally positioned and, for example, develops folds, whereby the tightness can be impaired and/or an increase in pressure can arise due to a reduction in the diameter, for example due to a congestion of the blood flow and/or thrombus formation caused by the folding. Such a thrombus formation can occur in particular in the region of the so-called dead zones of the folds and can represent a not inconsiderable risk, in particular when the thrombus becomes detached. Such problems can occur in particular with relatively long vascular implants, such as, for example, in the case of thoracoabdominal aneurysms. The vascular implant can have a length in a respective main direction of extension (in particular in a longitudinal direction along the vessel) of more than 3 cm, preferably of at least 5 cm, particularly preferably of at least 7 cm, for example for the treatment of such aneurysms.

The provision of at least one diameter change can also be of interest in the region of one or more iliac vessel grafts. For example, the diameter of a main liner body at the end of a bifurcation (e.g., at the end of the bifurcation in the direction of flow) can be larger or smaller than the diameter of the respective iliac vessel. The diameter of the main liner body (e.g., the diameter of the main liner body at the end of the bifurcation) can be adapted to the diameter of the iliac vessel in that the iliac vessel graft tapers (i.e., tapers in the direction of blood flow when the vascular implant is inserted in the aorta).

Diameter changes along one or more modules of the vascular implant can also be favorable for manufacturing purposes to facilitate the modular structure. For example, at a first end, a respective module can be adapted to the diameter of the vessel and, at a second end, to the diameter of a preceding or succeeding module. Moreover, at a first end, a respective module can be adapted to the diameter of a preceding module and, at a second end, to the diameter of a succeeding module.

In the course of the method, it can be determined whether a diameter change is desirable, for example by comparing the diameters of the vascular implant to be produced at the ends of the at least one tubular liner body and/or at different positions within the at least one tubular liner body, for example on the basis of the obtained vessel parameters. When this results in a deviation of at least 5 mm, preferably of at least 3 mm, particularly preferably of at least 2 mm, this can be used as a criterion that a diameter change is desirable and such a diameter change can be integrated, for example, into the computer-aided model of the vascular implant. In particular, this can be achieved by a uniform diameter change in the respective region of the vascular implant or also by a stepwise or jump-like diameter change. Combinations of these two possibilities are also conceivable for a particularly good fit of the vascular implant. A diameter change can be achieved, for example, by a reduction or increase in the used thread count, i.e., by a reduction or increase in the wale count and/or by an increase or reduction in the stitch density. Alternatively or additionally, a diameter change can be achieved after manufacturing the vascular implant, in particular by a step of thermoforming and/or heat setting the vascular implant on a mandrel.

Furthermore, it can be advantageous to provide one or more bifurcations and/or branches along the at least one tubular liner body of the vascular implant. This is particularly advantageous when the vessel section to be replaced has a branching itself and/or a branching in direct proximity and/or an artificial opening is to be made for the purpose of an anastomosis. The vascular implant can be positioned in an optimal and positionally stable manner in that the vascular implant also has a respective branching. Furthermore, by means of a vascular implant which, like the respective vessel section to be replaced, also has a branching, the respective function of the vessel section to be replaced as well as of the regions directly adjacent thereto, in particular transport of blood, can be restored and/or ensured after implantation of the vascular implant.

In the context of the present invention, a "bifurcation" of the vascular implant means a branching at one of the ends of the vascular implant, in particular a splitting of the vascular implant, preferably into two tubular liner bodies having comparable or similar diameters in particular at the splitting point and/or in direct proximity thereto. The two bifurcation liner bodies resulting from a bifurcation thus have respective diameters, at least at the splitting point and/or in direct proximity thereto, which differ from each other, for example, by at most 15%, preferably by at most 10%, particularly preferably by at most 5%, relative to the respective larger diameter. The two tubular liner bodies are preferably produced integrally with the vascular implant.

A "branch" of the vascular implant, on the other hand, is a branching along the at least one tubular liner body of the vascular implant, wherein the tubular liner body being provided or being in the main direction of extension of the vascular implant hereinafter can also be referred to as the main liner body for clarification purposes, and a tubular liner body branching off therefrom as the side liner body. The side liner body has a considerably smaller diameter than the main liner body at the splitting point and/or in direct proximity thereto, for example a diameter reduced by at least 25%, preferably a diameter reduced by at least 50%, particularly preferably a diameter reduced by at least 75%.

According to the invention, a recess is also provided along the at least one tubular liner body of the vascular implant. Such a recess can in particular be a fenestration and/or a scallop. A recess is particularly advantageous when the vessel section to be replaced comprises a branching itself and/or a branching in direct proximity. In this case, instead of branchings of the vascular implant such as bifurcations and/or branches, corresponding respective recesses can be provided, allowing a faster and less expensive production.

In the context of the present invention, the term "fenestration" refers to windows, open zones or holes in the vascular implant which, when the vascular implant is correctly positioned, are configured to be approximately, preferably entirely, congruent with a respective branching vessel in terms of position and diameter in the respective vessel section to be replaced.

In the context of the present invention, the term "scallop", on the other hand, refers to a recess at one end of the at least one tubular liner body. Preferably, the term scallop refers to a triangular, quadrangular, semicircular, oval or U-shaped recess at the end of the vascular implant, preferably the end that is located upstream in the direction of flow. Hence, a scallop is open towards the respective end of the vascular implant, in particular in the main direction of extension of the respective tubular liner body of the respective module.

Furthermore, structural elements also comprise one or more local reinforcements. In the context of the present invention, the term "local reinforcement" refers to reinforcement structures locally introduced into or to be introduced into the textile structure. They are particularly advantageous in that they enable a load-appropriate design of the vascular implant. Local reinforcements can comprise materials locally introduced into the textile structure of the vascular implant, such as yarns and/or wires, and/or reinforcement structures, each consisting of or comprising, for example, one or more yarns and/or wires. Optionally or alternatively, local reinforcements can comprise materials locally applied onto the textile structure, such as at least one polymeric structure, for example made of silicone. Local reinforcements are particularly preferably formed as local stitch construction changes, in particular to enable a load-appropriate design of the textile structure. In this way, a textile and/or textile-based vascular implant configured in a load-appropriate manner can also be integrally warp knitted, whereby it can be designed to be particularly resistant. Local reinforcements can also be configured as a combination of materials locally introduced into the textile structure of the vascular implant, materials locally applied onto the textile structure and/or changes in the stitch construction. Local reinforcements can be provided in and/or arranged in the textile surface of the vascular implant and/or at the transition from the textile surface of the vascular implant to a respective structural element selected from the group consisting of diameter change along at least one tubular liner body of a respective module, bifurcation, branch and recess. Thus, local reinforcements can be integrated into a vascular implant alone and/or in conjunction with one or more of the aforementioned structural elements.

Finally, structural elements also comprise one or more iliac vessel grafts. In the context of the invention, an "iliac vessel graft" refers to a graft which is usually separate when introduced into the body and which, during implantation (in the patient's body), can be connected to a bifurcation provided on the vascular implant. The iliac vessel graft also has a tubular liner body and preferably also a stent structure surrounding this tubular liner body. Such an iliac vessel graft can protrude into the iliac vessels via the native bifurcation and can be used in particular when a section of the iliac vessels is also to be bridged. An iliac vessel graft according to the invention has preferably a length of at least 3 cm, at least 5 cm, at least 7 cm or at least 10 cm. An iliac vessel graft can again include further structural elements such as diameter changes, recesses, bifurcations, branches and local reinforcements.

In particular, a combination of a local reinforcement and another structural element can be particularly advantageous. For example, a module can comprise a bifurcation and/or branch comprising at least one local reinforcement. The local reinforcement can be advantageous in particular at the transition from the tubular liner body to two tubular liner bodies or at the transition from the main liner body to the side liner body in order to ensure the tightness of the vascular implant and the required strength of the textile structure at the transition point. In the case of a fenestration, in particular at least one local reinforcement in the region of the fenestration located upstream and/or downstream in the direction of flow is advantageous in order to distribute the load over at least two threads and thereby ensure the resistance during the implantation and/or the fatigue strength of the fenestration. This can be achieved by a change in the stitch construction, for example by the use of a two-needle-overlap at the region of the fenestration located upstream and/or downstream in the direction of flow, particularly preferably in both regions. Alternatively or additionally, the two-needle overlap can be used across a plurality of courses and/or when binding the edges of the fenestrations in the warp knitted fabric of the liner body.

In the case of a manual input, the user can select one or more structural elements and optionally specify the desired position, geometry and/or further parameters relating to the respective structural element in the 3D model, the technical drawing, a 2D pixel file (e.g. a design file and/or a JC file) or the KMO file and/or have the respective parameters determined by means of a respective computer program. For this purpose, the respective computer program preferably comprises a query in the form of an input option. By means of the input option, the user can select, for example, one or more structural elements, for example in the form of a drop-down list, as well as optionally have respective parameters determined for each selected structural element by a respective computer program and/or enter them manually, preferably by means of a respective standardized input mask. Alternatively, the selection of the type and position of the one or more structural elements can be performed by means of a drag-and-drop function in the visualized 3D model. This allows an efficient query of respective parameters in a standardized format. Furthermore, the input option preferably also offers the possibility of not entering or selecting any structural element. The vascular implant can then be produced, for example after a final confirmation by the user.

Optionally, the respective computer program has a function by means of which the necessity of one or more structural elements can be automatically detected as well as respective structural elements selected and respective parameters optimally determined and integrated into the model. Such an automation reduces possible error sources and allows a time- and cost-efficient production of a patient-specific vascular implant. The detection can be performed, for example, by querying threshold values and/or data stored in a database, for example parameters relating to respective vessels, and matching them with the corresponding respective vessel parameters obtained. For example, a respective computer program can detect the necessity of a structural element when the distance between the vessel section to be replaced and a branching vessel falls below a certain minimum distance and/or the vessel section to be bridged or replaced comprises a branch. When the query of one or more structural elements and the determination of the respective parameters are performed automatically, the respective computer program preferably comprises a query regarding the user's approval of the proposed structural elements and/or parameters determined therefor, and optionally a possibility of correction by the user. This can take place, for example, after the necessity of at least one structural element has been detected and/or after the respective parameters have been determined. When no necessity of one or more structural elements is detected, the vascular implant can be produced on the basis of the created model immediately after a possible correction, but in particular after a final confirmation by the user.

After the query of one or more structural elements, respective specific parameters are integrated into the 3D model, the technical drawing and/or the 2D pixel file, in particular into the color-coded 2D pixel file, preferably automatically by means of a respective computer program, and the resulting model is optionally visualized. Preferably, the user can then make a correction, if necessary, and/or confirm the integrated structural elements with the respective parameters upon a visual inspection. Furthermore, the respective model is subsequently stored in a format readable by a respective machine for manufacturing the vascular implant, in particular a warp knitting machine, in particular in the form of a KMO file.

By means of the aforementioned steps of the method according to the invention the automatability, in particular a reduction of possible error sources, improved quality consistency of the vascular implants to be produced as well as time and cost efficiency can be improved, while at the same time maintaining full control by the respective user.

According to the invention, the vascular implant (e.g., the endovascular implant) is textile and/or textile-based. Techniques and materials known to the person skilled in the art can be used to create a textile, wherein the vascular implant is preferably made of biocompatible and/or hemocompatible materials. Examples thereof are polytetrafluoroethylene (PTFE), polyethylene terephthalate (PET), polyvinylidene fluoride (PVDF), polyurethane (PU), polylactide (PLA), polycaprolactone (PCL), ultra-high molecular weight polyethylene (UHMWPE) and/or liquid crystal polymer (LCP).

The vascular implant according to the invention is a woven fabric and/or a knitted fabric, preferably a knitted fabric. In this context, the term "woven fabric" is preferably understood to mean woven fabrics produced by interlacing at least two thread systems at right angles. The term "knitted fabric", on the other hand, refers to warp- and weft-knitted fabrics comprising one or more intertwined threads.

For example, monofilament and/or multifilament yarns can be used as threads for the production of the vascular implant. When multifilament yarns are used, the filament count is at least 22f, preferably at least 36f, particularly preferably at least 100f. With respect to the total titer of the filament, the filaments can have a fineness of 1 dtex up to and including 80 dtex, preferably up to and including 60 dtex, particularly preferably up to and including 50 dtex, for example according to EN ISO 2060:1995, preferably according to variant 1 mentioned in item 4, or in the case of monofilaments, for example according to EN 13392:2001. After its production, the vascular implant can, for example, have a material layer thickness of 0.01 mm to 2 mm, preferably of 0.1 mm to 0.5 mm, preferably optically measured in the product and/or preferably by means of a thickness measuring gauge.

The vascular implant according to the invention is preferably produced by means of the jacquard technique, particularly preferably by means of the jacquard double-face Raschel technique. The jacquard double-face Raschel technique allows a particularly flexible adaptation of the vascular implant to the respective patient anatomy.

The method according to the invention further preferably comprises the determination of positions of edge bindings. Since, according to the invention, the warp knitted fabric is preferably produced in two surfaces, edge bindings designate areas in which respective two surfaces are connected to each other, in particular parallel to the production direction of the warp knitted fabric production. Threads of the edge binding thus form stitches in each of the respective surfaces, wherein a tubular structure can be formed. Thus the respective at least one tubular main liner body of the at least one module of the vascular implant can have at least two edge bindings, by means of which the tubular structure of the respective module can be formed.

For the production of the vascular implant, a double-face Raschel machine with piezo jacquard technology is preferably used. A format readable by this machine is the KMO file. Therefore, the information of the created computer-aided model of the vascular implant is preferably electronically transferred to a respective machine, for example by means of a USB interface, particularly preferably as a KMO file comprising, if applicable, parameters of at least one structural element integrated into the model. Upon receipt of the information required for producing a patient-specific vascular implant in the form of a KMO file or another format readable by the machine, the vascular implant, e.g. endovascular implant, is produced.

The vascular implant according to the invention preferably has a density of stitches arranged in the production direction or a course density of more than 20 stitches per a unit length of 1 cm, preferably of more than 25 stitches per a unit length of 1 cm, particularly preferably of more than 30 stitches per a unit length of 1 cm measured in the final product. The stitches form thread interstices in the textile and thus form pores of the vascular implant. The size and the opening area of the pores are therefore well adjustable, for example a pore size from 1 μm to 1000 μm, more preferably from 10 μm to 300 μm, and/or an opening area of the pores from 1 to 1,000,000 μm², preferably from 100 to 90,000 μm². The pores of the vascular implant can be of the same size and/or a different size and can also vary, for example, with respect to their size along the at least one tubular liner body of the vascular implant. Thus, for example, a positionally stable positioning of the vascular implant in the vessel can be supported by ingrowth of native tissue into the pores.

The vascular implant can be configured to be permeable to fluids. In this case, the vascular implant preferably forms a self-sealing system, wherein the fluid transported and/or stored in the vessel seals the vascular implant after its implantation, for example by coagulation of components contained in a liquid in and/or on the vascular implant. To this end, for example, a pore size can be selected such that it can be sealed at the vascular implant upon implantation of the vascular implant in a blood vessel, for example, by a deposition of fibrin as part of blood clotting at the vascular implant. Alternatively, the vascular implant can be configured to be impermeable to fluids, for example by means of a coating with, for example, biocompatible silicone, polyurethane, collagen and/or gelatin.

In a further advantageous embodiment of the method according to the invention, the vascular implant (e.g. the endovascular implant) is integrally warp knitted. In other words, the method according to the invention for producing a vascular implant (e.g. an endovascular implant) is preferably further characterized in that it comprises integrally warp knitting the vascular implant comprising at least one module each comprising at least one tubular liner body and respective one or more structural elements. Preferably, for example, the two tubular liner bodies into which the vascular implant branches at the bifurcation are formed integrally with the preceding tubular section. The two tubular liner bodies of the bifurcation can be connected to the remaining tubular liner body of the respective module by means of a continuous warp knitted fabric (without separating threads), but separating threads can also be used if necessary. In the case of a branch, the main body and the side body are preferably integrally formed. The main body and the side body can be connected to each other by means of a continuous warp knitted fabric (without separating threads), but separating threads can also be used if necessary. Likewise, the one or more reinforcements, in particular when formed as a two-needle overlap, can be integral with the liner body, in particular integrally warp knitted.

Integrally warp knitting the vascular implant comprising the at least one module each comprising at least one tubular liner body and respective one or more structural elements can be performed in particular by the jacquard technique and offers several advantages. One advantage is that the vascular implant has no weak points due to manufacturing, as may be the case, for example, when sewing material edges. Another advantage is that further work steps are not required in the production of the vascular implant, such as, for example, in conventional methods, the incorporation of fenestrations and/or scallops by means of punching and/or cutting, for example by means of a cutting tool and/or laser.

In a further advantageous embodiment of the method according to the invention, in the case of a positive query of at least one structural element, the method comprises further steps depending on the at least one selected structural element to be integrated into the vascular implant to be produced, which will be explained in more detail below.

Preferably, when the vascular implant to be produced is to comprise one or more bifurcations and/or one or more branches, the method according to the invention further comprises the steps of: preferably determining the geometry and stitch construction at the transition from the main liner body to the at least one bifurcation and/or at least one branch; determining positions of separating threads; introducing separating threads during the production of the vascular implant (e.g., the endovascular implant); and separating the separating threads of the produced vascular implant.

In the context of the present invention, "separating threads" refer to individual wales which are not connected to other wales by an underlap, wherein an underlap refers to the connection of two adjacent stitches formed from the same thread. Stitches arranged one above the other in the direction of warp knitting are referred to as wales. The use of separating threads results in separating lines in the textile structure, which permit a defined cutting of the textile according to the respective specifications. Due to the design of the warp knitted structure when using separating threads, the risk of the textile structure coming undone or unravelling can thus be reduced and the formation of running stitches can be excluded by the choice of the stitch construction. Furthermore, the use of separating threads in combination with a change in the stitch construction, for example in order to incorporate recesses, local reinforcements, bifurcations, diameter changes and/or branches into a vascular implant, is particularly advantageous as it allows an integral production of a vascular implant (e.g. an endovascular implant) comprising at least one structural element selected from the group consisting of diameter change, bifurcation, branch and scallop. When the vascular implant is warp knitted with at least one separating thread, the regions of the warp knitted fabric adjacent to the at least one separating thread can preferably be configured with at least one local reinforcement, for example by a respective change in the stitch construction. This is advantageous in that a combination of separating threads and local reinforcement minimizes the risk of unravelling of the structure of the warp knitted fabric after separation of the separating threads. By means of the local stitch construction change, a front textile surface can be connected to a back textile surface to form a tube. The local stitch construction change can be different from the aforementioned edge bindings.

When the vascular implant to be produced is to comprise at least one bifurcation and/or branch and/or at least one diameter change, the method according to the invention comprises determining positions of the separating threads to be incorporated into the vascular implant. This is preferably done automatically by a respective computer program, particularly preferably in the context of determining respective parameters of the bifurcation and/or branch.

When at least one bifurcation has been selected, determined and/or entered as a structural element, the corresponding vascular implant can be integrally warp knitted by changing the stitch construction and/or using separating threads. For this purpose, the position and extension of the bifurcation are determined in a patient-specific manner on the basis of the obtained vessel parameters and, when separating threads are used, the position and extension of the bifurcation are determined in such a way that the tubular liner body of the vascular implant is divided in the warp knitting direction into two tubular liner bodies having, e.g., a comparable width when the warp knitted fabric is viewed in two dimensions or having, e.g., a comparable diameter when viewed in three dimensions, as defined. In the context of the present invention, the extension orthogonal to the main direction of extension of the warp knitted fabric is referred to as the width of the warp knitted fabric. In order to form a bifurcation, for example, the used thread count can be divided, uniformly or non-uniformly, between respective bifurcation liner bodies resulting from a bifurcation. Optionally or alternatively, threads can be removed or added to form a bifurcation. When the bifurcation liner bodies are integrally formed, the stitch construction is preferably locally changed. The tubular main liner body of the vascular implant can comprise two edge bindings, by means of which the tubular structure of the vascular implant can be formed, and the bifurcation liner bodies resulting from a bifurcation can each comprise two edge bindings, by means of which the tubular structure of the respective bifurcation liner body can be formed. At least one of the two edge bindings of the main liner body can merge into an edge binding of one of the bifurcation liner bodies, in particular without interruption. In particular, the two edge bindings of the main liner body can merge into a respective outer edge binding of one of the two bifurcation liner bodies, in particular without interruption.

When at least one branch has been selected, determined and/or entered as a structural element, the corresponding vascular implant is preferably integrally warp knitted, as in the case of a bifurcation. For this purpose, a unitary tubular liner body of the vascular implant can be subdivided in the region of the branch into a further tubular liner body (upstream or downstream of the branch in the warp knitting direction, depending on the procedure) and a tubular side liner body. For this purpose, a stitch construction change is preferably provided in the region of the branch. In this connection, the unitary tubular liner body, the further tubular liner body and the side liner body are preferably warp knitted in the same direction. Described in other words, during the warp knitting operation, the further liner body and the side liner body preferably extend parallel to the unitary liner body warp knitted upstream or downstream of the division. The further tubular liner body can have a smaller width, when the warp knitted fabric is viewed in two dimensions, or a smaller diameter, when the warp knitted fabric is viewed in three dimensions, than the tubular liner body.

Alternatively or additionally, the side liner body can be integrally produced by means of added threads. This refers in particular to threads which are not used for warp knitting the tubular main liner body, at least in the regions directly upstream and/or directly downstream of the respective branch. Preferably, when the tubular main liner body is warp knitted, a plurality of separating threads are provided (in the warp knitting direction upstream and/or downstream of the region of the branch) (wherein said separating threads can be warp knitted, for example, parallel to the main direction of extension of the main liner body). Preferably, the threads to be formed as separating threads are warp knitted parallel to the main liner body with the same stitch construction as the respective main liner body and are formed as separating threads directly adjacent to the respective branch. This enables a particularly high-quality fabric appearance and robust procedure. Using these separating threads, a side liner body is then warp knitted at a desired location, which is connected to the main liner body during warp knitting. Thus, a side liner body which originates from the main liner body at a desired position in the longitudinal direction of the main liner body can be warp knitted from the (preferably plurality of) separating threads. The side liner body can already be integrally produced during warp knitting at a desired angle to the main liner body (e.g., 0° to 75°, 5° to 75° or 10° to 75°, preferably 0° to 45°, 5° to 45° or 10° to 45°). The diameter of the main liner body can remain substantially constant throughout the region of the branch. Preferably, the side liner body is produced without reducing and/or splitting the thread count used for the main liner body. Optionally, the same separating thread or threads can be used at different locations along a respective module and/or the implant in order to form different structural elements, such as, for example, in order to form a plurality of branches or in order to form a branch and a bifurcation.

Irrespective of the method of production, the side liner body can have a smaller width or diameter than the further tubular liner body.

The previously determined position of the separating threads is integrated into the computer-aided model, preferably in particular into the color-coded 2D pixel file. According to the information integrated in the model, in particular with regard to arrangement on the tubular liner body and extension, the separating threads are introduced into the vascular implant (e.g. the endovascular implant) during its production. The vascular implant is thus warp knitted with separating threads according to the computer-aided model.

After the vascular implant has been produced, the separating threads contained in the vascular implant are preferably separated. The separation of the separating threads of the produced vascular implant can be performed by various methods known to the person skilled in the art, for example by cutting. Preferably, the separation of the separating threads is performed automatically, but it can also be performed manually.

In the method according to the invention, the one or more branches and/or bifurcations can be warp knitted parallel to the main direction of extension of the respective module and/or implant. The branch or bifurcation can be arranged at an angle to the main direction of extension by subsequent thermoforming and/or heat setting. Alternatively or additionally, the one or more branches and/or bifurcations can be warp knitted at an angle to the main direction of extension of the respective module and/or implant, in particular by using separating threads.

When the vascular implant to be produced is intended to comprise one or more recesses, the method according to the invention preferably further comprises the steps of: determining positions of at least one local reinforcement at the edges of the at least one recess and/or incorporating separating threads. When the at least one recess is intended to be a fenestration, the method preferably comprises the incorporation of at least one local reinforcement during the production of the vascular implant. When the at least one recess is intended to be a scallop, the method preferably comprises the determination of positions of separating threads, the incorporation of local reinforcements and the incorporation of separating threads during the production of the vascular implant as well as the separation of the separating threads of the produced vascular implant.

A recess in a vascular implant according to the invention particularly preferably comprises at least one local reinforcement at the edges of the at least one recess. Thus, a fenestration preferably comprises a local reinforcement in the region of the fenestration located upstream and/or downstream in the direction of flow, particularly preferably in both regions. A scallop preferably comprises a local reinforcement in the region of the scallop located downstream in the direction of flow. The corresponding parameters, in particular the respective position of the at least one local reinforcement, are preferably automatically determined and integrated into the computer-aided model of the vascular implant. Particularly preferably, a local reinforcement is configured by a change in the stitch construction, in particular by a two needle overlap (in particular at the upper and/or lower end). According to the parameters integrated in the model, the vascular implant is thus warp knitted integrally with local reinforcements according to the model.

When at least one recess is a scallop, the vascular implant can be integrally warp knitted using separating threads. For this purpose, the position and extension of the separating threads are determined in a patient-specific manner on the basis of the obtained vessel parameters in such a way that the stitches directly surrounding the at least one scallop are configured as stitches of respective separating threads. In this way, the region of the tubular liner body warp knitted at the location of the scallop can be removed after the production of the vascular implant. The incorporation of local reinforcements and the incorporation of separating threads during the production of the vascular implant as well as the subsequent separation of the separating threads can be carried out as already described.

When the vascular implant to be produced is intended to comprise one or more diameter changes, the method according to the invention preferably further comprises the steps of: determining parameters relating to thread tension, thread count, course density and/or stitch size. Alternatively or additionally, the method preferably comprises the steps of: determining positions of separating threads, incorporating separating threads during the production of the vascular implant (e.g., the endovascular implant), and separating the separating threads of the produced vascular implant.

Additionally or alternatively to the option of using separating threads as already described, a diameter change can be configured by changing parameters relating to thread tension, thread count, course density and/or stitch size. For example, a reduction in the diameter of the vascular implant can be achieved by increasing the thread tension, reducing thread count, for example by using separating threads, increasing the course density or reducing the stitch size, or from a combination of one or more of the aforementioned options. However, when an increase in the diameter is necessary, this can be achieved by reducing the thread tension, increasing the thread count, reducing the course density and/or increasing the stitch size.

The vascular implant according to the invention can comprise a plurality of modules, which are integrally warp knitted and are connected via separating threads. These modules can be separated from each other after warp knitting by separating the separating threads. For example, a tubular main liner body (optionally comprising one or more branches, one or more fenestrations, one or more scallops and/or one or more diameter changes) can form a first module and the bifurcation can be configured as a second module connected to the first module via separating threads. A tubular liner body for a graft to be inserted into the right iliac vessel can be a further module, and/or a tubular liner body for a graft to be inserted into the left iliac vessel can be a further module. The tubular liner body or bodies for the iliac vessel graft or grafts can be connected to the first module, in particular to the ends of the bifurcation, via separating threads.

Alternatively, the main tubular liner body (optionally comprising one or more branches, one or more fenestrations, one or more scallops and/or one or more diameter changes) can form a first module directly comprising a bifurcation (i.e. without the main tubular liner body and the bifurcation being separated after the warp knitting operation) and a further module can be formed by a tubular liner body for a graft to be inserted into the right iliac vessel and/or a further module can be formed by a tubular liner body for a graft to be inserted into the left iliac vessel.

The tubular liner body or bodies for the iliac vessel graft or grafts can be connected to the first module, in particular to the ends of the bifurcation, via separating threads. According to a further alternative, a tubular main liner body (optionally comprising one or more branches, one or more fenestrations, one or more scallops and/or one or more diameter changes) can form a first module, and a graft to be inserted into one of the iliac vessels can form a second module, which is connected to the first module via separating threads during warp knitting. The different modules are preferably expanded in an overlapping manner in the body, whereby they are connected.

When the vascular implant according to the invention is intended to comprise at least one iliac vessel graft, the iliac vessel graft is preferably warp knitted integrally with the remaining vascular implant and subsequently separated from the remaining vascular implant in order to be separately insertable into the body. This allows for a cost-efficient production of patient-specific iliac vessel grafts. In particular, the length and/or diameter of the graft can be determined as a patient-specific parameter. Depending on the individual anatomical requirements of the patient, the iliac vessel graft can be formed with a constant diameter or with one or more diameter changes. Furthermore, an iliac vessel graft can have at least one recess and/or at least one branch.

In order to achieve easy separability of the iliac vessel graft from the remaining vascular implant, an integrally warp knitted iliac vessel graft is preferably connected to the remaining graft via separating threads. For example, in particular one end of the integrally warp knitted iliac vessel graft can be connected to one end of a bifurcation liner body integrally warp knitted with the remaining vascular implant via separating threads. The separating threads are then separated after the warp knitting operation in order to provide an iliac vessel graft that is separately insertable into the patient's body.

In a further advantageous embodiment of the method according to the invention, the method further comprises the following steps: obtaining pre-operative medical image data of a vessel; visualizing the obtained image data; identifying a vessel section for which a vascular implant (e.g., an endovascular implant) is to be produced; and measuring vessel parameters. Even though standardized vascular implants (in particular standardized endovascular implants) can be produced by means of the method according to the invention, it is preferably used to produce individualized vascular implants. In this way, the patient-specific anatomy in the affected section can be particularly well taken into account. This is advantageous in particular in the case of branchings of the vessel section to be replaced, since the configuration and position of the branching can greatly vary. Therefore, the vascular implant is preferably produced on the basis of image data of at least the vessel section for which a vascular implant (e.g., an endovascular implant) is to be produced. In particular, the structure and/or shape of the vascular implant, such as, for example, the position, shape and/or size of one or more structural elements, can be designed and/or produced in a patient-specific manner on the basis of such image data.

Therefore, pre-operative medical image data of at least the vessel section to be replaced are preferably obtained in the course of the method according to the invention, preferably of at least the vessel section to be replaced including directly adjacent vessel sections. The image data are preferably obtained by means of computed tomography or magnetic resonance tomography, but optionally also by means of X-ray or ultrasonic devices, especially when they are suitable for recording and/or creating a 3D image data set. As a basis for the production of an individualized vascular implant, the image data preferably comprise a slice thickness of at most 3 mm, preferably at most 2 mm and particularly preferably at most 1 mm. The data are preferably acquired in the longitudinal direction of the body, i.e. from cranial (headwards) to caudal (tailbonewards) or in the reverse direction at a distance of 0.05 mm to 10 mm, preferably at a distance of 0.5 mm to 3 mm. Two successive slices can have an overlap of at most 50%, preferably at most 25%, wherein the distance between the slices is at most as great as the corresponding slice thickness. In order to ensure high-quality information with respect to the exact configuration of the vessel wall, the acquired and/or obtained images are preferably post-processed in a manner known to the person skilled in the art, for example by means of multiplanar reconstruction, in order to provide a spatial resolution as high as possible in all spatial directions, before they are used for the production of an individualized vascular implant.

The gathered and/or provided image data can have been created at one or more points in time and, in a preferred method according to the invention, are used to produce a computer-aided model of the vascular implant in order to configure an individualized vascular implant.

Preferably, the obtained pre-operative medical image data are further visualized. A visual representation of the data facilitates the control of the obtained data quality as well as the completeness of the obtained data. In the event of data quality insufficient for the creation of a computer-aided model or in the event of incomplete data, the user can thus be warned, for example, alternatively or additionally by the output of a respective notice. In this way, the renewed obtaining of pre-operative medical image data of the vessel section to be replaced as well as of the vessel sections directly adjacent thereto can be promptly initiated, wherein the provision of a patient-specific vascular implant can take place in a particularly time-efficient manner.

The method according to the invention can further comprise identifying, preferably automatically, a vessel section for which a vascular implant (e.g., an endovascular implant) is to be created. The vessel section to be replaced is identified on the basis of the obtained image data preferably by means of a method implemented in a computer-aided program. However, this can also be done manually by an appropriate marking and/or input by the user. Preferably, however, the identification is performed automatically, for example by an automatic segmentation of the vessel to be treated and/or matching of gray values. Furthermore, for example, matching with entries of a database containing threshold values for respective vessel parameters can be performed. In addition, if available, patient-specific vessel parameters that the vessel segment to be replaced exhibited before the vessel wall alteration occurred can be used for comparison. This enables maximum patient-specific adaptation of the vascular implant to be produced.

Preferably, the vessel section to be replaced is also visually output in the visualization of the image data. In this way, the user can check the automatically identified vessel section and, if necessary, correct it, for example lengthen, shorten, widen or restrict it. A query as to whether the user agrees to proceed with the method according to the invention can be provided and accordingly implemented in the respective computer program.

Once the vessel section to be replaced has been identified, and preferably also confirmed by the user, the measurement of respective vessel parameters of the vessel section to be replaced is preferably performed. For this purpose, for example, a centerline of the vessel to be treated can first be determined, which can optionally also be regarded as the axis of rotation of at least one of the tubular liner bodies of the vascular implant to be produced in accordance with its main direction of extension. However, a centerline can also be determined deviating from a midline of the vessel to be treated, for example to take into account mechanical properties of devices used for an implantation of the vascular implant and/or mechanical properties of the vascular implant itself. Furthermore, vessel parameters can be measured by means of the obtained medical image data and optionally with the aid of the determined midline of the vessel to be replaced, such as the length and diameter of the vessel as well as the location, angle and diameter of vessel branchings. Such parameters can subsequently be used to calculate parameters of the vascular implant, such as the length and diameter of the one or more liner bodies and/or the location and diameter of recesses. In addition to such geometric parameters already described, morphological parameters can optionally be captured, such as the presence of thrombi and/or calcification as well as the respective location, geometry and extension.

The measured vessel parameters are preferably stored and provided for the creation of the computer-aided model of the vascular implant, as already explained. The measured vessel parameters can in particular also be analyzed in the determination of structural elements such as local reinforcements and accordingly integrated into the model of the vascular implant (e.g., the endovascular implant).

When the vascular implant to be produced is a stent graft and/or a valve implant, such as for example a heart valve, the method according to the invention in a further advantageous embodiment preferably further comprises applying a stent structure onto the produced textile and/or textile-based vascular implant and/or a valve at the produced vascular implant. In this context, the term "stent structure" or also "stent" refers to a structure which preferably comprises a plurality of struts and is configured in a tubular and/or tube-shaped manner. In this context, a stent structure, just as a valve, is preferably made of a biocompatible material, in particular a biocompatible polymer-based material, but can alternatively, for example, also be made of metal and/or comprise metal. In particular in the case of a stent structure, this stent structure is preferably designed to be patient-specific, taking into account measured vessel parameters, in particular geometric as well as optionally also morphological vessel parameters. For example, a visualization in particular of the created 3D model of the vascular implant to be warp knitted, and thus of the graft, can also be advantageous for a further product design following the textile manufacturing, such as for example a suitable positioning of a stent structure. In the visualized model, the positioning of a stent structure can be easily performed and, for example, a technical drawing for the design and layout of the stent and for the subsequent assembly of graft and stent can be generated therefrom. Additionally, a simulation of the implantation and/or the behavior of the vascular implant under mechanical stress, such as during or after an implantation, can be advantageous for an optimal design of a stent structure of a stent graft. The application of a stent structure and/or the attachment of a valve to a graft produced according to the invention can be carried out in various ways known to the person skilled in the art, for example by means of suturing, gluing, welding or fusing.

In a further advantageous embodiment of the method according to the invention, the stent structure is printed onto the produced vascular implant. In this case, the stent structure is preferably made of a polymer-based, in particular biocompatible, material and the application of the stent structure onto the vascular implant, in this case a so-called graft, is carried out by means of an additive process, in particular by means of fused deposition modeling. In the context of the present invention, the term "additive process" includes additive manufacturing processes or processes for additive and/or generative manufacturing which are known to the person skilled in the art and in which elements are automatedly produced by attaching material on top of each other and/or joining it to each other. Additive processes comprise, for example, 3D printing processes as well as processes in which fused material is deposited layer by layer, such as fused deposition modeling. In fused deposition modeling, the material of the stent structure is liquefied, for example, by a heated nozzle and applied onto the graft in the form of filaments in one or more layers, preferably immediately and/or directly onto the graft. The material can be supplied to the nozzle as a filament.

Preferably, the stent structure is applied onto the graft by using a rotatable holder by means of which the graft can be held and/or rotated, preferably around its longitudinal axis. Such a holder can be, for example, a rotating tubular mandrel and/or a rotating tubular scaffold, on the outer surface of which the provided graft rests. In this case, the at least one stent structure is preferably applied externally onto the graft. Provided that the applied stent structure is to be arranged inside the graft, the method according to the invention can comprise a further optional step of inverting the stent graft. Thus, the graft of the stent graft according to the invention can be provided to encase the stent structure from the inside or the outside.

In a further advantageous embodiment, the method according to the invention further comprises steps of shaping and/or fixing the vascular implant (e.g. the endovascular implant) by means of a heat treatment and/or heating the produced vascular implant (e.g. the produced endovascular implant). In other words, the method according to the present invention preferably comprises a step of thermoforming and/or heat setting the vascular implant, e.g. endovascular implant, in particular in the case of one or more diameter changes along the tubular liner body. In the context of the present invention, heat setting occurs after a respective textile fabrication. Further, in the context of the present invention, the term thermoforming refers to shaping the textile by a combination of a respective mandrel geometry of the holder and heat influence, in particular heat influence of at least 120° C. or at least 150° C. A step of thermoforming and/or heat setting is particularly advantageous for maintaining and/or fixing the shape of the implant after production. In this step, the shape of the woven or warp knitted implant can in particular also be further adapted to the shape of the vessel to be treated. For example, the shape of the one or more recesses can be adapted, in particular expanded. Alternatively or additionally, the angle of bifurcations and/or branches relative to the main direction of extension of the implant can be adapted and fixed. Alternatively or additionally, in particular the respective diameter of the one or more liner bodies can be adapted, in particular expanded. Moreover, the shape of the vascular implant at the transition from the main liner body to one or more bifurcation liner bodies and/or side liner bodies can be fixed in a desired shape (e.g., in a rounded and/or stepless shape) by thermoforming and/or heat setting. Thus, an optimal, patient-specific design of the vascular implant can be achieved by a step of shaping and/or fixing the vascular implant, e.g. endovascular implant, alone and/or in combination with adjustment options regarding the production of the warp knitted fabric, such as stitch construction and incorporation of at least one structural element as described above.

For shaping and/or fixing, the produced vascular implant is preferably held by a holder, which is preferably rotatable and/or turnable, preferably around its longitudinal axis. The holder preferably has at least one diameter corresponding to that of the vessel section to be replaced. In order to produce diameter changes by thermoforming and/or heat setting, the holder can also comprise regions having different diameters (e.g. diameter jumps).

Particularly preferably, a holder is used which comprises at least one mandrel having a respective mandrel geometry according to the created computer-aided model of the produced vascular implant. Thus, a holder can have a modular structure (e.g., by connecting different holder sections having different diameters and/or by connecting a main section for fixing the main liner body with bifurcation sections and/or branch sections for fixing bifurcations and/or branches of the produced graft). A respective holder can be created, for example, by means of additive manufacturing or on the basis of machining processes using the created computer-aided model of the produced vascular implant. This has the advantage that holders with a mandrel geometry can be created and used quickly and cost-savingly which enable an optimal shaping of the produced vascular implant with respect to the respective patient anatomy and/or the fixation of this very shape in order to ensure the function of the vascular implant. Such a holder can be, for example, a rotating tubular mandrel and/or a rotating tubular scaffold on the outer surface of which the vascular implant rests. The holder can be configured as a solid body. Preferably, however, the holder is a hollow mandrel, preferably having thin walls. Irrespective of whether the holder is formed as a solid body or with a hollow mandrel, the holder optionally has branches according to the branches incorporated in the graft. A thin-walled, hollow mandrel is particularly advantageous since it can ensure homogeneous heat conduction and thus ensure uniform thermoforming and/or heat setting of the applied vascular implant. Preferably, the holder is made of stainless steel and/or comprises stainless steel. The holder can also consist of and/or comprise different materials; the holder can comprise, for example, an aluminum alloy which can be surrounded by a PTFE film. Surface irregularities can thus be reduced and a smooth surface of the holder ensured.

The vascular implant can thus be placed onto a holder and/or clamped thereonto with a defined pre-stretch, wherein the defined pre-stretch can be, for example, 20%, preferably 30%. Particularly preferably, a defined pre-stretch is locally adapted taking into account respective textile parameters and/or by means of a respective mandrel geometry of the holder. The holder is then heated together with the vascular implant placed thereon according to material-specific predefined parameters and/or holder-specific predefined parameters, for example according to the respective material, the respective geometry and/or the respective design of the at least one mandrel, for example as a hollow or a solid mandrel, in particular temperature and duration, preferably in an oven, particularly preferably in a dry air oven. Subsequently, the holder together with the vascular implant placed thereon is removed, for example from the oven, preferably cooled at room temperature and the vascular implant is taken off, for example by pulling it off the respective holder. By the controlled heat treatment of the vascular implant in the course of the thermoforming and/or heat setting step, a controlled shrinkage of the vascular implant in its main direction of extension or the warp knitting direction of the textile and/or textile-based vascular implant can take place and/or be fixed. Such a shrinkage entails that in particular recesses are brought into their respective intended geometry, in the case of produced fenestrations, for example, from warp knitted slits into respective oval or circular openings. Particularly advantageously, a vascular implant warp knitted with a main liner body having a constant or substantially constant width (when viewed in 2 dimensions) and/or a constant or substantially constant diameter (when viewed in 3 dimensions) can be provided with different diameters and/or diameter jumps, in particular along the main liner body, by means of thermoforming and/or heat setting after warp knitting.

After the shaping and/or fixing step, parameters of the vascular implant can again be compared with measured parameters of the vessel section to be treated and/or specific parameters of the model. In this way, an optimal fit of the patient-specific vascular implant for the vessel section to be replaced can be confirmed.

In a further advantageous embodiment of the method according to the invention, the method further comprises steps for refining the vascular implant (e.g., the endovascular implant), for example by means of "coating" or the application of a layer of, for example, biocompatible gelatin and/or collagen. This can be particularly advantageous when the vascular implant is to be impermeable to fluids.

Furthermore, in an advantageous embodiment, the method according to the invention preferably comprises a step of sterilizing the produced vascular implant (e.g., the produced endovascular implant).

In an advantageous embodiment of the method according to the invention, the described method steps are preferably performed by at least one computer program. Should more than one computer program be used, the method according to the invention additionally comprises the following steps for each change of the computer program: optionally translating the information, such as, for example, the model of the vascular implant, into a format which can be read by the respective following computer program, optionally storing the information in the respective format, transferring the information in the format which can be read by the respective following computer program to the respective computer program, and reading the obtained information by the respective computer program. Optionally, moreover, one or more outputs to the user can be provided before and/or after one or more of the aforementioned steps, in particular outputs such as error messages and/or queries relating to a storage of the information and/or transfer of the information to the respective following computer program. In particular, the use of a single computer program at least for the method steps described in connection with the measurement and determination of vessel parameters as well as the computer-aided model is advantageous, since the efficiency of the method can thus be maximized.

A query as to whether the user agrees to proceed with the method according to the invention can be made after each of the described steps of the method. Likewise, a storage of the respective data can take place during and/or after each of the described steps.

A second aspect of the invention relates to a vascular implant, which can in particular be an endovascular implant. The vascular implant is preferably produced using the method of the invention according to the first aspect of the invention. However, the vascular implant according to the invention is not limited to the use of this method. In this respect, the invention also relates to a vascular implant comprising any one of the structural elements described above, irrespective of how they are produced. The features and advantages resulting from the method according to the first aspect of the invention are to be taken from the description of the first aspect of the invention, wherein advantageous embodiments of the first aspect of the invention are to be regarded as advantageous embodiments of the second aspect of the invention and vice versa.

In the following, some particularly preferred embodiments of the vascular implant according to the invention (e.g., the endovascular implant) are described by way of example, without limiting the scope of protection of the invention. Details of structural elements of the individual embodiments described in the following are to be understood as details of respective structural elements of other embodiments, even if not explicitly mentioned. The person skilled in the art will appreciate that the respective structural elements are to be provided depending on the patient anatomy and thus any combinations of these structural elements are encompassed.

In an advantageous embodiment of the vascular implant according to the invention, the vascular implant comprises at least one diameter change along at least one tubular liner body of a respective module. A diameter change can thereby be configured, starting from a specific end of the tubular main liner body, as a taper or a widening of the tubular main liner body in its respective main direction of extension. For example, the vascular implant can comprise one or more stepwise diameter changes. Alternatively, the vascular implant can comprise one or more continuous diameter changes extending over at least 5%, at least 10%, at least 20%, at least 30%, at least 40% or even at least 50% of the length of the vascular implant in its main direction of extension. The vascular implant can also comprise more than one diameter change along at least one tubular liner body of a respective module, such as two, three, four or five. For example, the vascular implant can comprise two diameter changes, wherein (i) the vascular implant has a larger diameter in a central section compared to the respective diameter of the terminal sections, (ii) the vascular implant has a smaller diameter in a central section compared to the respective diameter of the terminal sections or (iii) the vascular implant has a central section exhibiting a diameter having a value that ranges between the respective values of the diameters of the terminal sections.

In a further advantageous embodiment of the vascular implant according to the invention, the vascular implant comprises at least one bifurcation. The vascular implant can comprise, for example, a bifurcation, wherein the bifurcation can be located in a middle section or in a terminal section of the vascular implant. For example, the vascular implant can comprise a bifurcation configured such that, with respect to the main direction of extension of the vascular implant, the section of the tubular liner body of the respective module without the bifurcation corresponds to, for example, up to 50%, up to 60%, up to 70%, up to 80%, up to 90% or up to 95% of the length of the vascular implant. Further, the two bifurcation liner bodies into which the main liner body splits at the bifurcation can each have a length of at least 0.5 cm, at least 1 cm, at least 2.5 cm or at least 5 cm, measured in their respective main direction of extension. The at least two liner bodies resulting from the one liner body can have the same, a comparable or different length, measured in their main direction of extension. In this case, a different length means a length that differs by at least 10%, at least 20% or even at least 30%, measured at the longer of the two or the longest of the bifurcation liner bodies resulting from the main liner body.

In a further advantageous embodiment of the vascular implant according to the invention, the vascular implant comprises at least one branch along a respective tubular liner body of a module of the vascular implant. For example, the vascular implant can comprise one branch, wherein the branch can branch from the main liner body in a central section or in a terminal section thereof. For example, the vascular implant can comprise a branch that branches from the main liner body with respect to the main direction of extension of the vascular implant at a distance from a terminal end of the main liner body that is at least 5%, at least 10%, at least 20% or at least 30% of the length of the vascular implant. For example, the vascular implant can also comprise two or more branches, wherein the branches can have equal or different distances to a terminal end of the main liner body measured in the main direction of extension thereof. When the vascular implant comprises two or more branches, the branches can extend from the main liner body at the same or different angles with respect to the main direction of extension thereof. Moreover, the at least two branches can branch from the main liner body such that the respective branch locations are arranged with respect to the main liner body on a straight line parallel to the central axis of the main liner body in the main direction of extension thereof and/or offset with respect to each other in the circumferential direction of the main liner body. Further, the at least one branch can have a length of the side casing body of at least 0.3 cm, at least 0.5 cm, at least 1 cm, at least 2.5 cm, or at least 5 cm, measured in the main direction of extension thereof.

In a further advantageous embodiment of the vascular implant according to the invention, the vascular implant comprises at least one recess, wherein the at least one recess can be configured as at least one scallop and/or at least one fenestration. The at least one scallop preferably has a recess height from 3 mm to 20 mm, preferably from 5 mm to 15 mm, measured in the direction of flow. The at least one scallop preferably has a recess width from 2 mm to 15 mm, preferably from 5 mm to 12 mm, more preferably from 7 mm to 12 mm, preferably measured transversely to the flow direction or in the circumferential direction. The at least one fenestration is preferably oval or round, particularly preferably with a height-to-width ratio between 0.5 and 2.5, preferably between 0.8 and 2, particularly preferably between 1 and 1.35. The at least one fenestration is preferably formed in a central region of the vascular implant, for example at a distance from an end of the vascular implant corresponding to at least 5%, at least 10% or at least 30% of the length of the vascular implant. Alternatively or optionally, the at least one fenestration is preferably configured such that it is at a distance from the nearest end of the vascular implant of at least 2 mm, at least 5 mm or at least 7 mm. The vascular implant can also comprise two or more recesses, for example one fenestration and one scallop, two fenestrations, two scallops, two fenestrations and one scallop, one fenestration and two scallops, three fenestrations, three scallops, three fenestrations and one scallop, or two fenestrations and two scallops. When the vascular implant comprises two or more recesses, their respective positions with respect to the tubular liner body can be arranged in a straight line extending parallel to the central axis of the liner body in the main direction of extension thereof and/or offset with respect to each other in the circumferential direction of the liner body and/or distributed around the circumference of the liner body but at the same position along the longitudinal axis of the liner body.

In a further advantageous embodiment, the vascular implant according to the invention comprises at least one local reinforcement. Preferably, the vascular implant comprises local reinforcements in regions where the liner body splits into two bifurcation liner bodies or into a main liner body and a side liner body, and/or in regions of the warp knitted fabric which delimit a recess, in particular in regions of a scallop and/or a fenestration that are terminal in the warp knitting direction. In the case of a fenestration, preferably both regions that are terminal in the warp knitting direction comprise a local reinforcement. In the case of a scallop, preferably at least the region located at the greatest distance from an end of the vascular implant comprises a local reinforcement. The reinforcement can be provided in particular by a spatially limited stitch construction change, in particular a spatially limited two needle overlap.

In a further advantageous embodiment of the vascular implant according to the invention, the vascular implant comprises at least one diameter change and at least one local reinforcement, wherein the at least one local reinforcement can be located in a section of a diameter change or not.

In a further advantageous embodiment of the vascular implant according to the invention, the vascular implant comprises at least one bifurcation and/or branch and at least one local reinforcement, wherein the at least one local reinforcement can be located in the at least one bifurcation and/or branch, in the region of the transition from the liner body into the at least one bifurcation and/or branch, or also in other regions of the liner body.

In a further advantageous embodiment of the vascular implant according to the invention, the vascular implant comprises at least one recess and at least one local reinforcement, wherein at least one recess is configured with at least one local reinforcement. The particularly preferred regions of the local reinforcements in the case of a fenestration and a scallop are to be understood as already indicated above. For example, the vascular implant can comprise at least one recess without a local reinforcement as well as at least one recess with at least one local reinforcement as described above. Preferably, all recesses of the at least one recess comprise a respective local reinforcement. Optionally, the vascular implant can comprise local reinforcements in further regions.

In a further advantageous embodiment of the vascular implant according to the invention, the vascular implant comprises at least one diameter change and at least one bifurcation, wherein the at least one bifurcation can be located in a section of a diameter change or not. For example, the vascular implant can comprise at least one diameter change and one bifurcation, wherein the at least one diameter change can be located in the liner body and/or in at least one of the two liner bodies resulting from the bifurcation. Optionally, the vascular implant can comprise local reinforcements in regions as described above and/or in further regions of the vascular implant.

In a further advantageous embodiment of the vascular implant according to the invention, the vascular implant comprises at least one diameter change and at least one branch, wherein the at least one branch can be located in a section of a diameter change or not. For example, the vascular implant can comprise at least one diameter change and one branch, wherein the at least one diameter change can be located in the at least one main liner body and/or in the at least one side liner body. Optionally, the vascular implant can comprise local reinforcements in regions as described above and/or in further regions of the vascular implant.

In a further advantageous embodiment of the vascular implant according to the invention, the vascular implant comprises at least one diameter change and at least one recess, wherein the at least one recess can be located in a section of a diameter change or not. The at least one diameter change and/or the at least one recess can comprise at least one local reinforcement, in particular the at least one recess. For example, the vascular implant can comprise at least one recess without a local reinforcement as well as at least one recess with at least one local reinforcement as described above.

In a further advantageous embodiment of the vascular implant according to the invention, the vascular implant comprises at least one bifurcation and at least one branch. The at least one bifurcation and/or the at least one branch can comprise at least one local reinforcement.

In a further advantageous embodiment of the vascular implant according to the invention, the vascular implant comprises at least one bifurcation and/or branch and at least one recess, wherein at least one recess is preferably configured with at least one local reinforcement. Preferably, the main liner body of the vascular implant comprises the at least one recess, but optionally one of the bifurcation liner bodies and/or side liner bodies resulting from a bifurcation can also comprise at least one recess, preferably with at least one local reinforcement each. For example, the vascular implant can comprise at least one recess without a local reinforcement as well as at least one recess with at least one local reinforcement as described above.

In a further advantageous embodiment of the vascular implant according to the invention, the vascular implant comprises at least one diameter change, at least one bifurcation and at least one branch, wherein the at least one bifurcation and/or the at least one branch can be located in a section of a diameter change or not. For example, the vascular implant can comprise at least one diameter change, one bifurcation and one branch, wherein the at least one diameter change can be located in the liner body, in at least one of the bifurcation liner bodies resulting from the bifurcation, and/or in the at least one side liner body. Optionally, the vascular implant can comprise local reinforcements in regions as described above and/or in further regions of the vascular implant.

In a further advantageous embodiment of the vascular implant according to the invention, the vascular implant comprises at least one diameter change, at least one bifurcation and/or branch and at least one recess, wherein in particular at least one recess is preferably configured with at least one local reinforcement. Preferably, the tubular liner body of the vascular implant comprises the at least one recess, but optionally one of the liner bodies and/or side liner bodies resulting from a bifurcation can also comprise at least one recess, preferably with at least one local reinforcement each. For example, the vascular implant can comprise at least one recess without a local reinforcement as well as at least one recess with at least one local reinforcement as described above.

A vascular implant according to the invention, e.g. an endovascular implant, can be configured, for example, as a stent graft. The term "stent graft" as used herein preferably refers to a stent structure comprising a graft attached thereto and thus comprises any type of vascular implants, in particular endovascular implants, which at least temporarily comprise at least one preferably tubular structure comprising a plurality of struts and at least one preferably polymer-based material layer as a sheath component. The stent graft can be configured for the treatment of aneurysms. In particular, a stent graft according to the invention can be a stent graft for the treatment of aortic aneurysms, such as, for example, for treating aneurysms of the thoracic, thoracoab-dominal or abdominal aorta. The produced textile and/or textile-based structure can thereby form the graft. The stent can be attached to this graft according to any method, but preferably after the graft has been produced by means of the additive and/or generative methods described.

The stent structure preferably comprises a plurality of struts connected to each other, wherein the struts have a height of at least 0.01 mm, preferably at least 0.05 mm or at least 0.1 mm, in a cross-section perpendicular to the direction in which the respective strut extends in the radial direction of the stent graft. For example, the struts can have a height from 0.01 mm to 3 mm, preferably from 0.05 mm to 1 mm. Alternatively or additionally, the struts can have a width perpendicular to the height in this cross-section of at least 0.01 mm, preferably at least 0.05 mm or 0.1 mm. For example, the struts can have a width from 0.01 mm to 3 mm, preferably from 0.05 mm to 1 mm. In particular, in the case of wire-based struts and/or wire structures as the stent structure, the struts and/or wire structures can have a diameter of at least 0.1 mm, preferably of at least 0.3 mm or 0.5 mm, in a cross-section perpendicular to the respective direction of extension.

The struts can be arranged in configurations known to the person skilled in the art, for example in zigzag-shaped and/or meander-shaped rings (crowns), spirally and/or in zigzag-shaped spirals. The spirals and/or rings can in turn be connected to each other via connectors. The struts can be provided such that in the expanded state they cover at most 50%, at most 40%, at most 30%, at most 20%, at most 12%, at most 10%, at most 8%, at most 6%, at most 5% or at most 3% of the outer skin surface of the graft. Further, the struts can be provided such that in the expanded state they cover at least 12%, at least 10%, at least 8%, at least 5%, at least 3% or at least 1% of the outer skin surface of the graft.

Preferred embodiments of the invention are described in the following by way of example with reference to the drawings. The drawings are merely schematic representations which, in order to clarify certain aspects, do not depict other (optional) structures where appropriate, or also take into account various optional, interrelated aspects in one representation. Identical reference signs indicate equivalent, similar, comparable or identical elements in the illustrated embodiments.

The illustrated embodiments can be modified in many ways within the scope of protection of the claims. The disclosure of the Figures is not intended to limit the scope of protection of the invention. It is to be noted that the features of the above embodiments can be combined in a single embodiment. Therefore, depending on the respective configuration, embodiments of the invention can comprise all or only some of the aforementioned features.

FIG. 1 shows as a schematic flow diagram the steps of a method 100 according to the invention for producing a vascular implant, which can be, for example, an endovascular implant 1.

Figure 1:
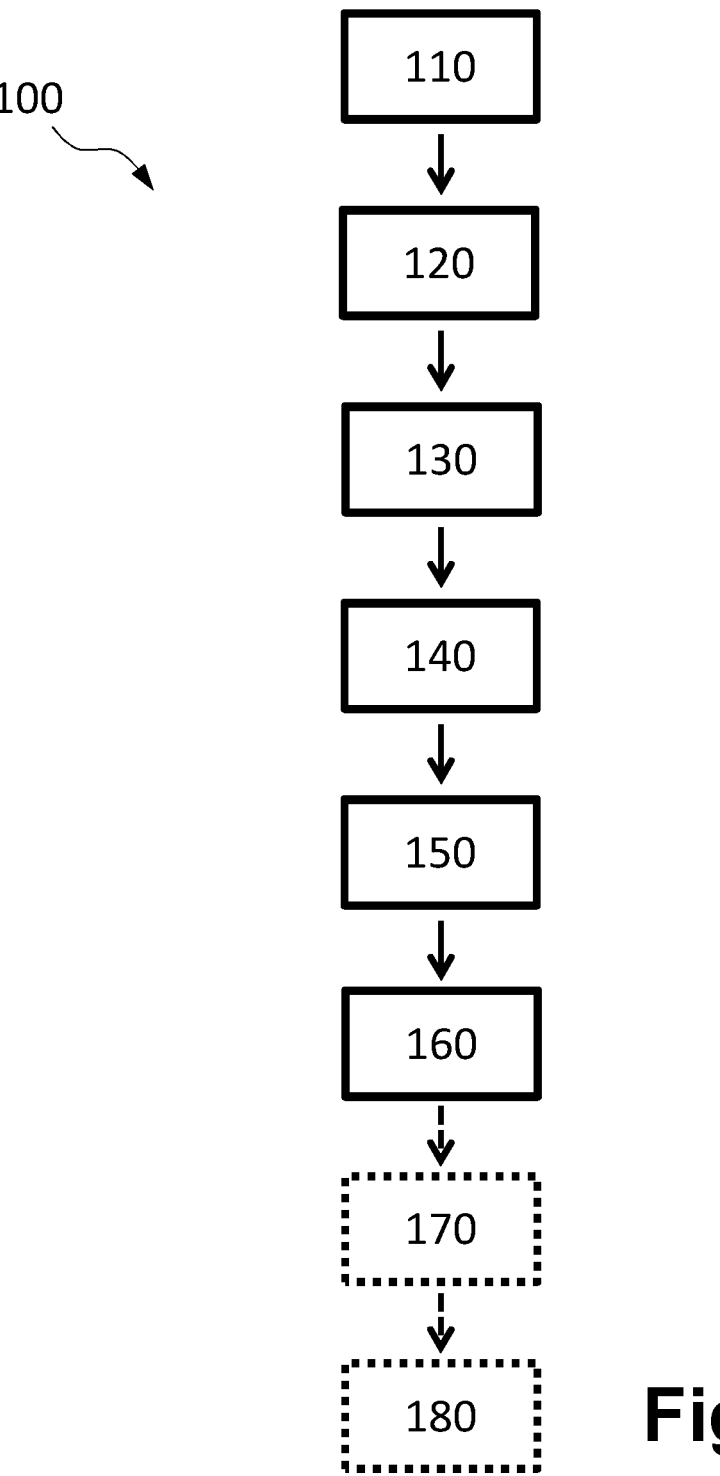
FIG. 1 shows a schematic flow diagram of a method according to the invention.

In a preferred embodiment of the method, firstly vessel parameters are obtained (step 110). These vessel parameters have preferably been obtained on the basis of pre-operative medical image data of a vessel, which have been gathered, for example, in the course of computed tomography and/or magnetic resonance tomography. The patient-specific image data can be processed in various ways known to the person skilled the art in order to obtain a preferably 3-dimensional resolution as high as possible. In order to obtain the vessel parameters, the image data are preferably visualized, the vessel section for which an endovascular vessel implant 1 (see FIG. 2) is to be produced is identified and the respective vessel parameters are measured, such as, for example, the position, diameter and extension of the vessel section to be bridged and/or replaced, as well as the position and geometry of anatomical features, such as branches and bifurcations of the vessel, are captured.

According to a preferred embodiment of the method 100, obtained vessel parameters (step 110) are used to create a computer-aided model of the endovascular implant 1 (step 120). The computer-aided model of the vascular implant 1 can be visualized, for example, for ease of use as well as for visual inspection.

In order to ensure an optimal fit of the vascular implant 1 after its insertion into the respective vessel, it is then queried whether one or more structural elements are relevant for this purpose (step 130). Such structural elements can be, for example, one or more diameter changes 10 along a tubular main liner body 2 of the vascular implant 1, one or more bifurcations 20, one or more branches 30 along a tubular liner body 2 of the vascular implant 1, one or more recesses 40, 50 along the liner body 2 and/or one or more local reinforcements 60 (see FIG. 2 and FIG. 5). The query can be made manually, for example by means of an input mask, or automatedly, for example by a comparison with respective vessel parameters stored in a corresponding database. When a positive query is made about at least one of the structural elements, the respective parameters are determined (step 140). This can also be implemented by a manual input, but preferably the determination is performed automatically or partially automatically by a respective computer program. Thereupon, the respective structural elements are integrated into the computer-aided model (step 150) based on the respective determined parameters. The computer-aided model can be at least a technical drawing, a design file, a JC file, and/or a KMO file, wherein preferably a digital 3D model is created and directly or indirectly converted into a machine-readable KMO file. An automated conversion of the model data into machine data is also possible.

Based on the created computer-aided model, the production (step 160) of the textile and/or textile-based and preferably individualized vascular implant 1 according to the invention is finally carried out by means of the jacquard technique on the basis of the created file which can be read by a respective warp knitting machine, preferably a KMO file. Subsequently, thermoforming and/or heat setting of the vascular implant 1 (step 170) and/or application of a stent structure (step 180) can optionally be performed.

Figure 2:
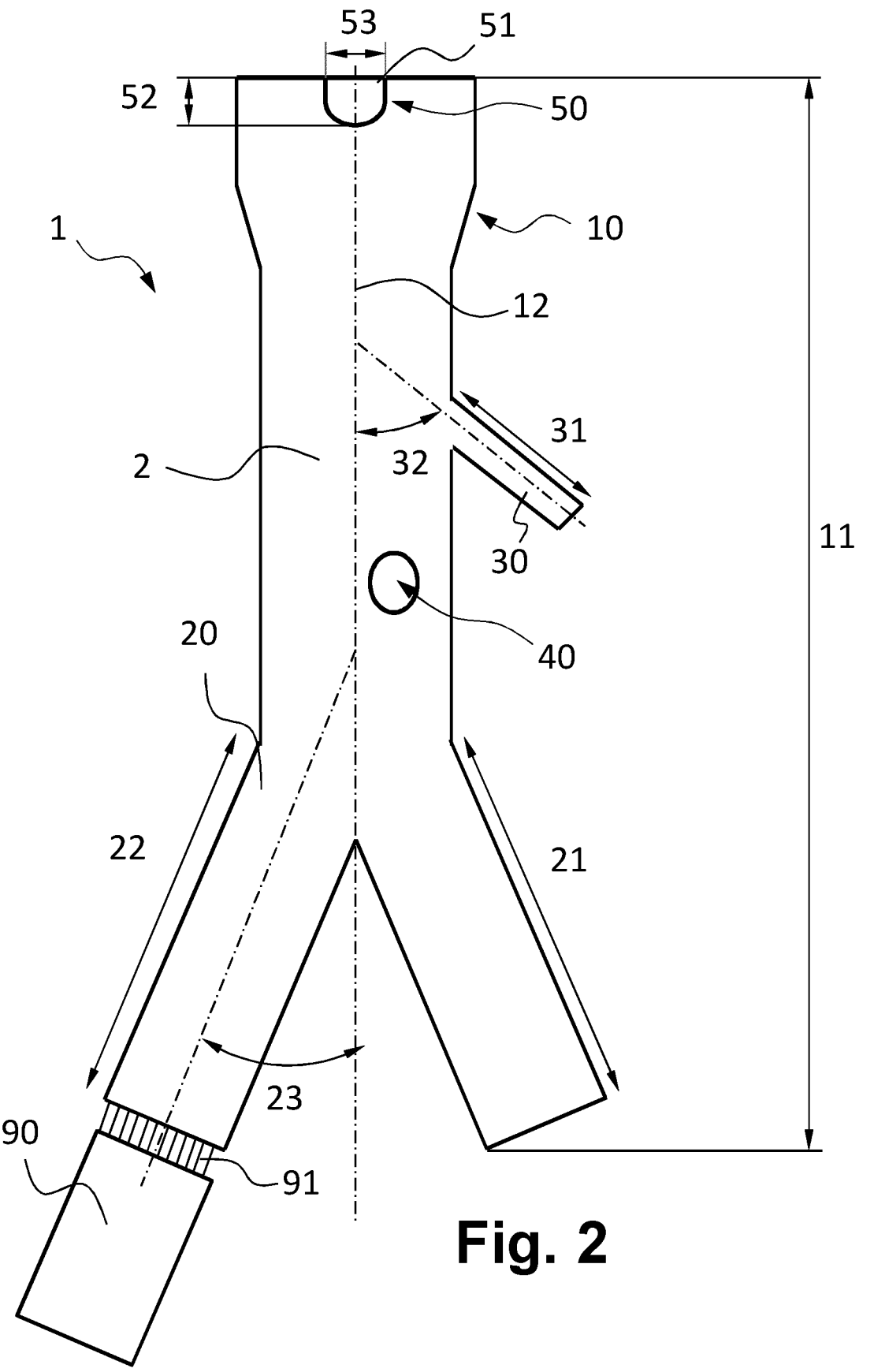
FIG. 2 shows a schematic representation of a vascular implant comprising various structural elements.

FIG. 2 shows a schematic representation of a vascular implant 1 comprising various structural elements according to the invention. The vascular implant 1 exemplarily illustrated in this Figure is formed as a graft and comprises structural elements formed integrally with the liner body of the graft. As shown, the structural elements are a diameter change 10 along the tubular liner body 2 of the vascular implant 1, a bifurcation 20, a branch 30 along the tubular liner body 2 of the vascular implant 1, and two recesses 40, 50, wherein one recess is formed as a fenestration 40 and one recess is formed as a scallop 50. The scallop 50 has an open end 51.

As further shown, the vascular implant 1 can have a length (i.e., overall length) 11 along its main direction of extension 12. The bifurcations 20 can have a respective bifurcation length 21, 22. The side liner body of the branch 30 can have a length 31 measured from the origin at the main liner body 2. FIG. 2 further shows that the bifurcation liner bodies are preferably each arranged at an angle 23 (shown only for the liner body 22) with respect to the main liner body. The side liner body is preferably arranged at an angle 32. The angles 23 are, for example, 0 to 75, preferably 0 to 45. Depending on the individual patient anatomy, the angles 23 can also be different within said ranges. The angle 32 is preferably 0 to 180, in particular 2 to 170. The scallop 50 has a recess height 51 from 3 to 20 mm, preferably from 5 to 15 mm, and/or a recess width 53 from 2 to 15 mm, preferably from 7 to 12 mm.

In the region of a bifurcation 20, one or two iliac vessel grafts 90 can be formed during warp knitting the vascular implant 1. Since iliac vessel grafts 90 are typically inserted into the body separately from the tubular liner body 2, the iliac vessel grafts 90 are preferably connected to a respective end of the bifurcation 20 via separating threads 91 during warp knitting so that the iliac vessel grafts 90 can be separated from the remaining tubular liner body 2 and the bifurcation 20 after the warp knitting operation is complete. In this connection, the iliac vessel graft or grafts 90 are preferably formed with a desired diameter progression, such as, for example, a desired constant diameter or with one or more diameter jumps or diameter change progressions, depending on the anatomical requirements of the specific patient. Appropriate diameter changes can be achieved by thermoforming as described above, alternatively or additionally also by the use of fewer or additional threads and/or the choice of the parameters. The iliac vessel grafts can include at least one branch and/or at least one recess, depending on patient-specific anatomical requirements.

The depicted structural elements are to be understood as purely exemplary. Therefore, depending on the design of the vascular implant 1, one or more of said structural elements can be formed, one or more of each type of structural element, as well as at different positions with respect to the liner body of the vascular implant 1 as described above. Preferably, the at least one structural element is configured in each case in a patient-specific manner.

Figure 3:
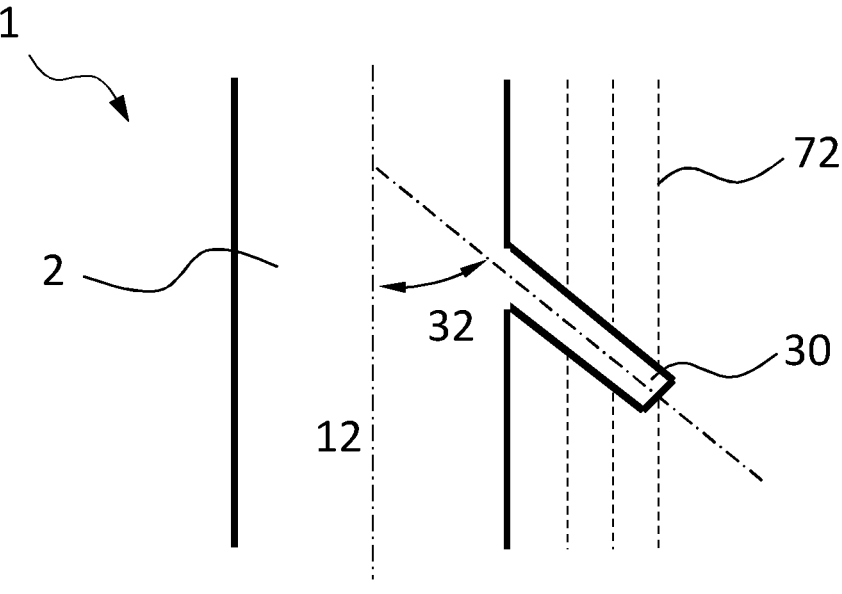
FIG. 3 shows a schematic representation of the integral warp knitting of a branch oblique to the main extension axis of the vascular implant.

FIG. 3 shows a detail of FIG. 2 and, in particular, schematically an integral configuration of the side liner body at the branch 30 oblique to the main extension axis 12 of the vascular implant 1. As illustrated in FIG. 3, for the oblique configuration of the branch in the warp knitting process 30, preferably separating threads 72 are used, preferably wales without an underlap, which are separated (e.g., by mechanical cutting or laser cutting) upon completion of the warp knitting process. The angle 32 at which the branch 30 projects from the main liner body 2 can be further adjusted, if necessary, in an optional thermoforming and/or heat setting step 170 (see FIG. 1) upon completion of the warp knitting process.

Figure 4:
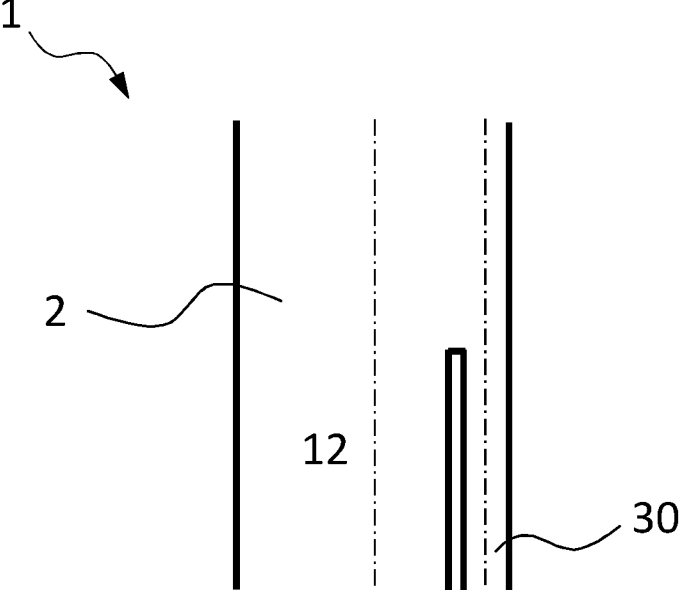
FIG. 4 shows a schematic representation of the integral warp knitting of a branch substantially parallel to the main extension axis of the vascular implant.

FIG. 4 schematically shows a further integral embodiment of the side liner body at the branch 30 with the main body 2. In this case, the side liner body is warp knitted substantially parallel or parallel to the main extension axis 12 of the vascular implant 1. Upon completion of the warp knitting process, the angular position of the side liner body can optionally be adapted to the vessel to be treated by a thermoforming and/or heat setting step 170 (see FIG. 1). In the case of this substantially parallel or parallel warp knitting of the side liner body with respect to the main extension axis 12, separating threads can be omitted. Optionally, however, separating threads can also be used in this context.

Although FIGS. 3 and 4 each show the production of a branch 30, the corresponding methods can equally be used to produce a bifurcation 20 of FIG. 2.

Figure 5:
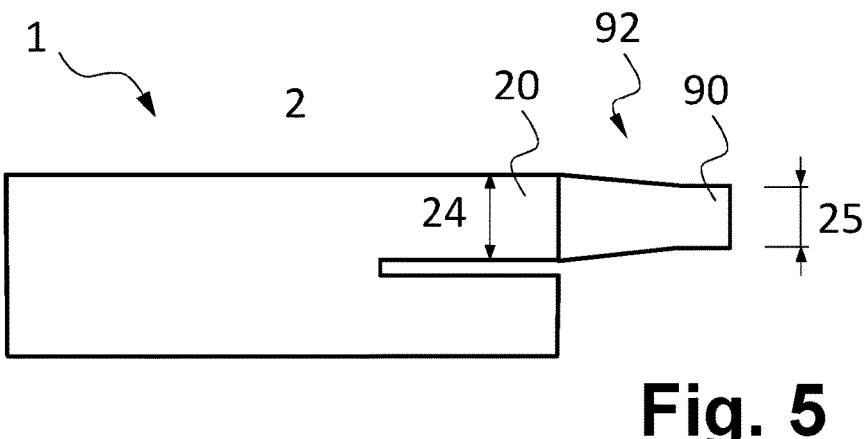
FIG. 5 shows a schematic representation of a diameter change in the region of an iliac vessel graft.

FIG. 5 shows the vascular implant 1 comprising a bifurcation 20, wherein an iliac vessel graft 90 is provided at the end of the bifurcation 20. As schematically illustrated, the bifurcation 20 can have a diameter 24 at its end facing away from the rest of the main liner body 2—i.e., at the end facing the iliac vessel graft. Since this diameter 24 can be chosen to be larger than the diameter of the iliac vessel and/or larger than a desired diameter 25 at a downstream end of the iliac vessel graft 90 for manufacturing reasons and/or in order to facilitate the implantation in the patient, it can be advantageous to provide at least one diameter change 92 along the iliac vessel graft 90. In this manner, the diameter of the iliac vessel graft 90 can be reduced to the diameter 25 desired for the iliac vessel. In FIG. 5, the diameter of the iliac vessel graft 90 decreases in the direction of blood flow. However, the diameter of the iliac vessel graft 90 could also increase in the direction of blood flow. The diameter 24 of the main liner body 2 could therefore also be smaller than the diameter 25 at the end of the iliac vessel graft 90 facing away from the main liner body 2, if necessary. It will also be apparent to the person skilled in the art that corresponding configurations can also find use at other body locations. The graft or grafts 90 can therefore be also grafts for other vessels.

Figure 6:
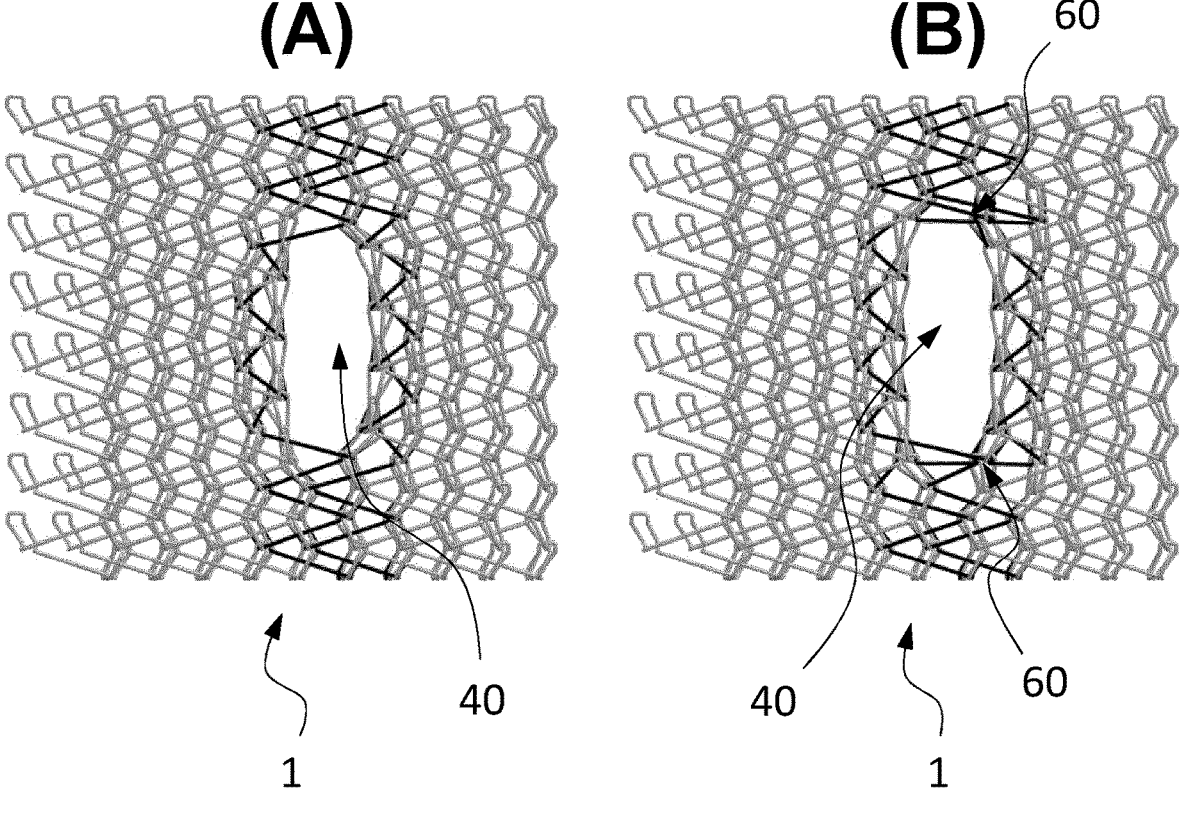
FIG. 6 shows a schematic illustration of a fenestration with a load-appropriate stitch construction change.

FIG. 6 schematically shows a fenestration 40 without (A) or with (B) a local reinforcement 60 by means of a load-appropriate stitch construction change by means of the use of a two-needle overlap 60. The course of the thread without (A) or with (B) two-needle overlap 60 is shown in black. As is revealed by the comparison of (A) and (B), the two-needle overlap 60 exemplarily shown in FIG. 6 allows the tensile load to be divided from one thread (A) to two threads (B) running in the circumferential direction.

Figure 7:
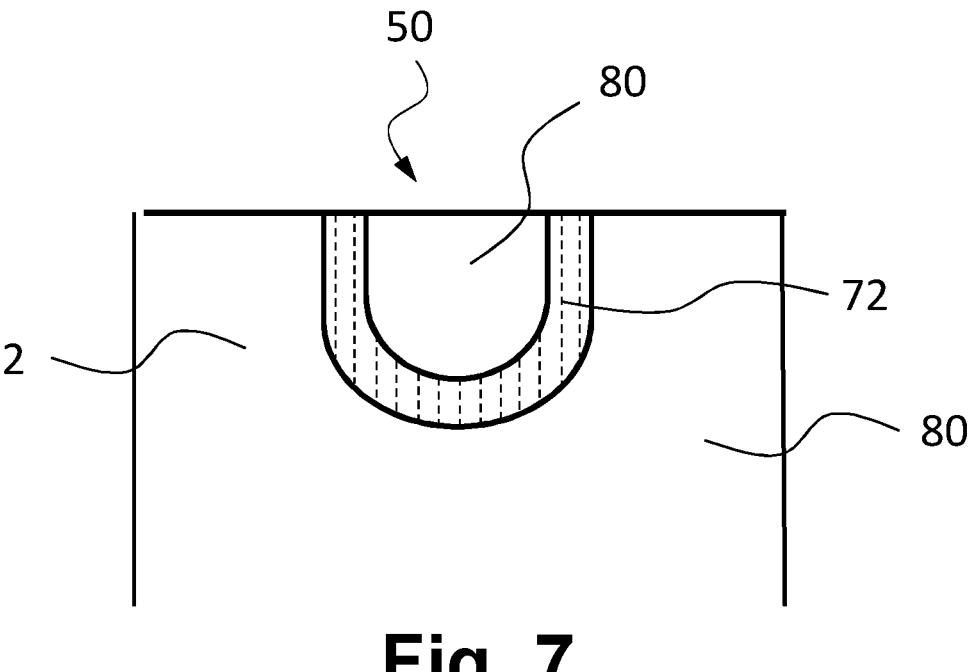
FIG. 7 shows a schematic representation of the warp knitting of a scallop with separating threads.

FIG. 7 schematically shows a possible configuration of the scallop 50 of FIG. 2. In this configuration, separating threads 72, i.e. preferably wales without an underlap, are provided between a section with an underlap 80 and the remaining main liner body 2 (warp knitted with an underlap). The separating threads 72 are subsequently separated so that the section with an underlap is removed from the scallop 50, and the scallop 50 forms an opening in the main liner body 2. Alternatively, the section with an underlap 80 can be replaced by longer separating threads 72. In this configuration, the section with an underlap 80 can also be referred to as a basic stitch construction 70.

Figure 8:
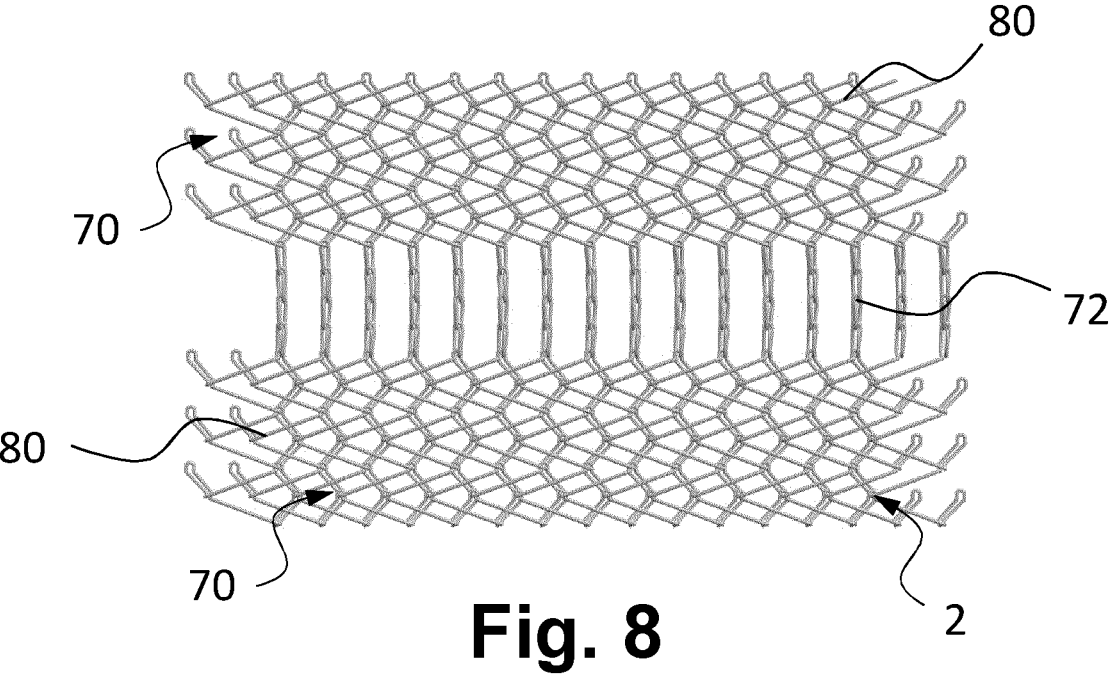
FIG. 8 shows a schematic representation of a warp knitted fabric with and without an underlap.

FIG. 8 shows a schematic detailed view of the section with an underlap 80 and its connection to the main liner body 2 (warp knitted with an underlap). As shown, in the context of the present invention, the separating threads 72 can in particular be formed as wales without an underlap.

Figures 9, 10:
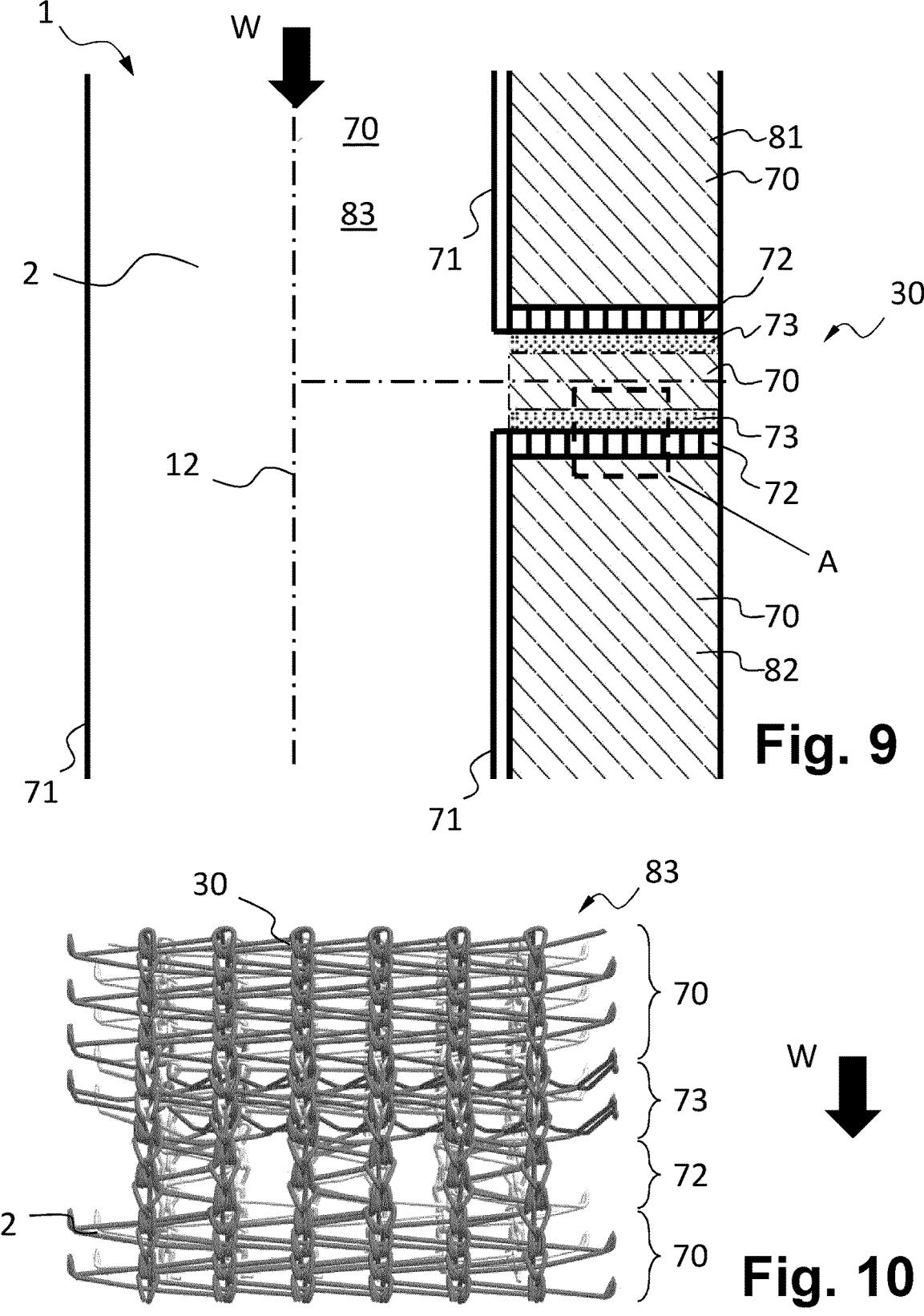
FIG. 9 shows a schematic representation of the integral warp knitting of a branch transverse to the main extension axis of the vascular implant.
FIG. 10 shows an exemplary stitch construction sequence during warp knitting the branch of FIG. 9 (front view)
Figure 13:
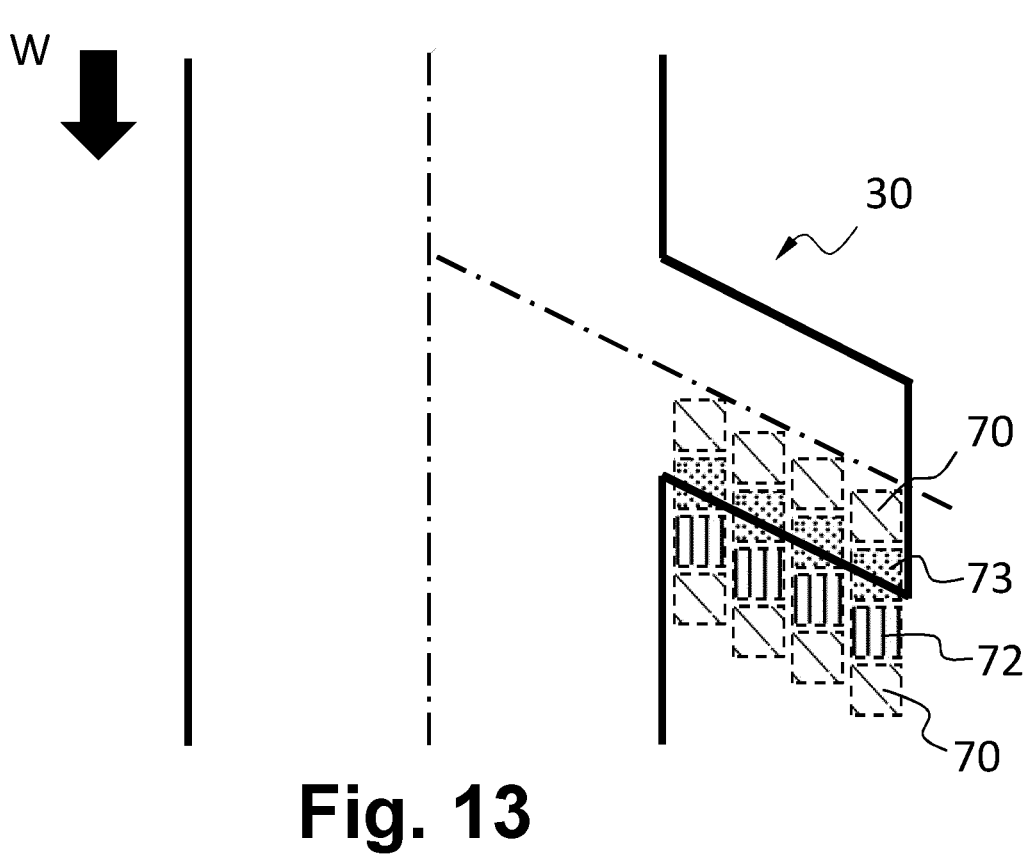
FIG. 13 shows a further schematic representation of the integral warp knitting of a branch oblique to the main extension axis of the vascular implant.
Figure 14:
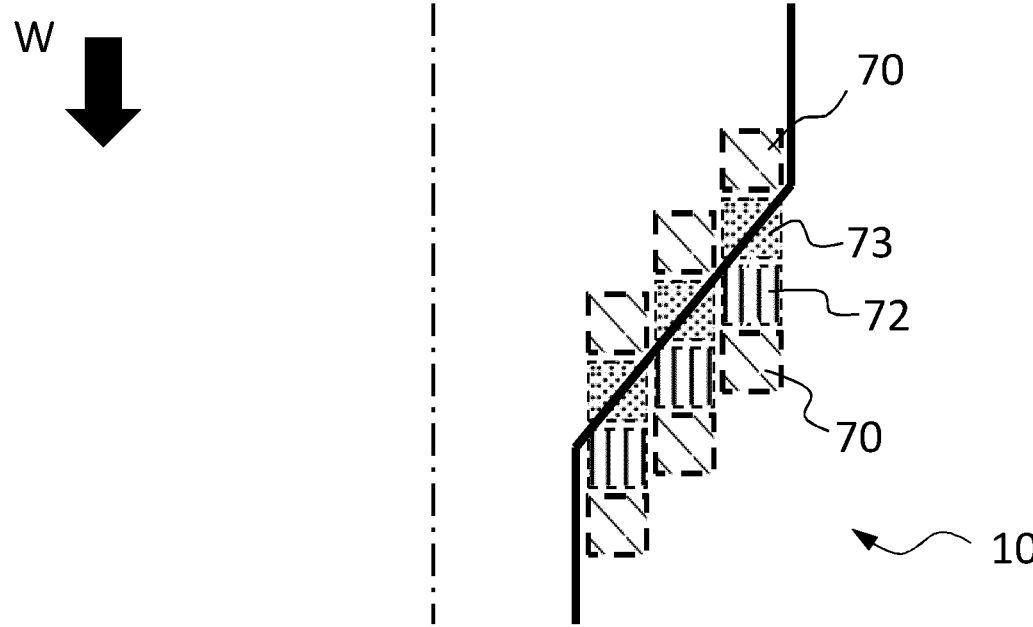
FIG. 14 shows a schematic representation of the integral warp knitting of a diameter change of the vascular implant.

FIG. 9 exemplarily shows a further possible stitch construction sequence in the case of integrally warp knitting various structural elements of the vascular implant 1, exemplarily shown in this Figure at a branch 30 which is arranged substantially perpendicularly to the main direction of extension 12 of the main liner body 2 (although this is merely for the purpose of better illustration and a corresponding stitch construction sequence can also be used in connection with other arrangements of the branch 30 or other structural elements, see also FIGS. 13 and 14).

In this connection, the main liner body 2 is warp knitted with a front textile surface 83 and a back textile surface 84 (not visible in FIG. 9), both having a basic stitch construction 70. The basic stitch construction 70 of the front and back textile surfaces can optionally coincide.

The stitch construction 70 of the front textile surface 83 and the back textile surface 84 are connected to each other along at least one edge region (in FIG. 9 along two edge regions) by an edge binding 71, resulting in the tubular main liner body 2. Edge bindings can be used in particular when the front and back textile surfaces 83, 84 are connected parallel to the production direction W. The threads for producing the branch 30 run along during the production of the main liner body 2, as already shown in FIG. 3, but in the variant of FIG. 9 they are formed in sections as a basic stitch construction 70 (schematically illustrated in FIGS. 9, 13 and 14 with an oblique hatching). In this way, a better process stability of the warp knitting process can be achieved. This results in a first section 81, which in the production direction W is upstream of the branch 30, and a second section 82, which in production direction W is downstream of the branch 30, wherein a basic stitch construction 70 can be present in each of these sections.

The first section 81 and the second section 82 are removed after the vascular implant 1 has been warp knitted. The basic stitch construction 70 of the sections 81, 82 transitions into separating threads 72 in an area adjacent and/or contiguous to the branch 30. This helps to prevent the warp knitted structure from unravelling. In addition, the sections 81, 82 can thus be separated more easily.

The branch 30 itself is provided, for example, by a further section comprising a base stitch construction 70, wherein again a front textile surface and a back textile surface are also provided in this section. The front textile surface and the back textile surface can each be formed as a continuation of the front textile surface 83 and/or the back textile surface 84, which are provided in the region of the main liner body 2. The basic stitch construction 70 along the branch 30 can thus correspond to that of the front textile surface 83 and/or to that of the back textile surface 84 of the main liner body 2. The respective underlap can extend from the main liner body 2 into the branch 30.

As further schematically shown in FIG. 9, a local stitch construction change 73 can be provided in each case along the branch 30 adjacent and/or contiguous to the separating threads 72. The front and the back textile surfaces 83, 84 are connected by the local stitch construction change 73. In this way, a tubular structure is formed in a simple manner in the region of the branch 30.

Figures 11, 12:
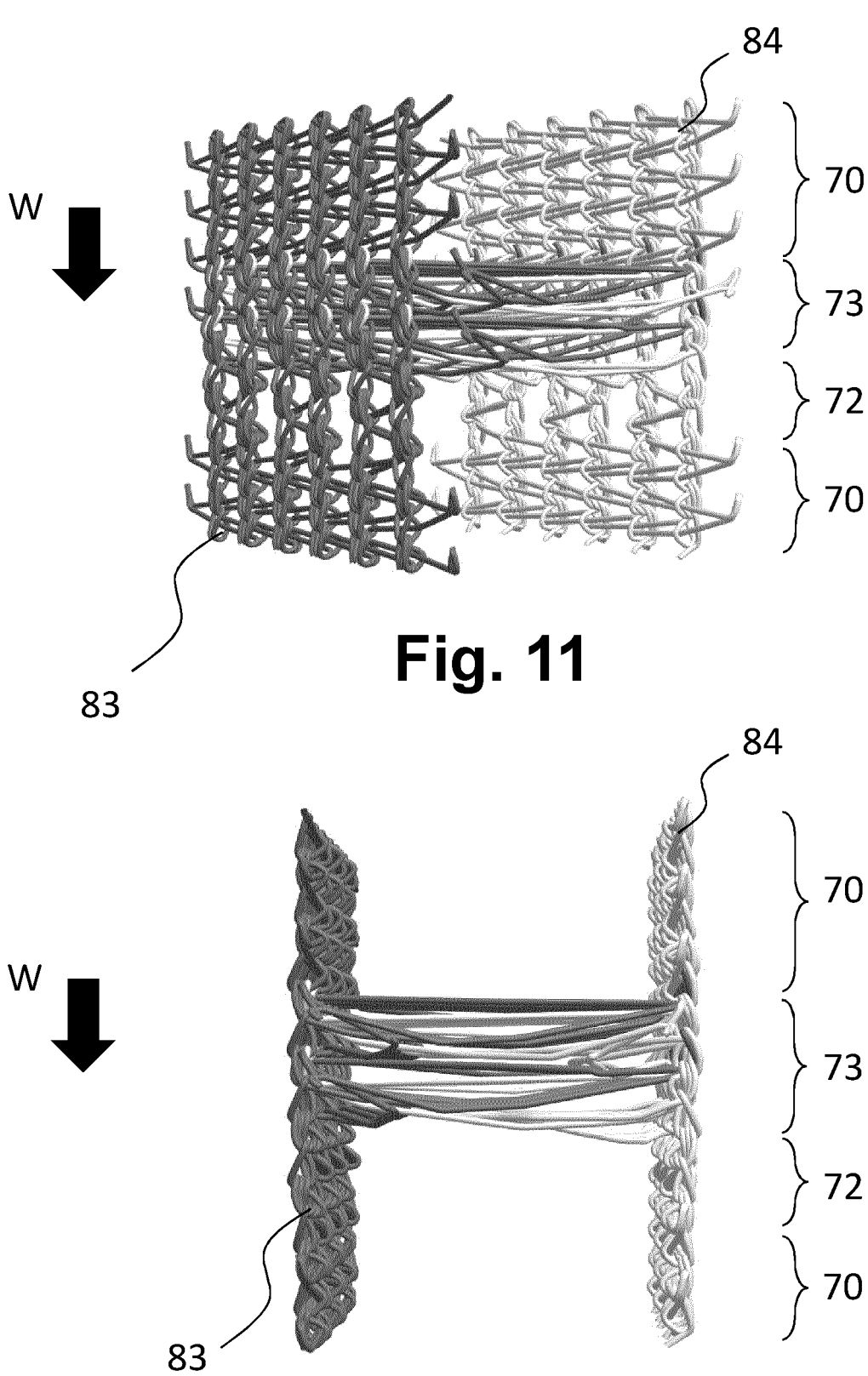
FIG. 11 shows the stitch construction sequence of FIG. 10 obliquely from the side.
FIG. 12 shows the stitch construction sequence of FIG. 10 in a side view.

FIGS. 10 to 12 schematically show detail A of FIG. 9 and thus a warp knitted fabric with the described stitch construction sequence along the front textile surface 83 and the back textile surface 84. Seen in the production direction W, a first area with basic stitch construction 70 (along the branch 30) is followed by a local stitch construction change 73, by which the front textile surface 83 and the back textile surface 84 are connected in order to produce a tube. This stitch construction change 73 is followed by separating threads 72, which prevent the warp knitted fabric structure from unravelling and facilitate the separation of the excess material from the branch 30 (and thus from the vascular implant 1) upon completion of the warp knitting process. Subsequently, the front and back textile surfaces 83, 84 can be again configured (at least in sections) with a basic stitch construction 70 along the section 82 that is separated upon completion of the warp knitting process.

The stitch construction arrangement of FIGS. 10 to 12 shows the area of detail A of FIG. 9 and thus the end of the branch 30 in the production direction W (i.e., the second edge area in the production direction W). However, it will be apparent to the person skilled in the art that a corresponding stitch construction arrangement can also be provided at the beginning of the branch 30 in the production direction W (i.e. at the first edge area in the production direction W), in particular a weave change in the reverse order.

The use of local stitch construction changes 73 in conjunction with separating threads 72 is particularly advantageous when the front and rear textile surfaces 83, 84 are to be connected at an angle other than parallel to the production direction W.

FIGS. 9 to 12 exemplarily show a stitch construction arrangement for an integrally warp knitted branch 30, in which the branch 30 and/or its side liner body originates from the main liner body 2 at an angle of about 90°. In this arrangement, as shown in the Figures, the local stitch construction change 73 and the transition to the separating threads 72 can be substantially perpendicular to the production direction W (i.e., horizontally in FIGS. 9 to 12 and/or in the case of conventional warp knitting machines).

However, the shown stitch construction change and/or stitch construction sequence is not limited thereto. For example, a corresponding stitch construction change and/or stitch construction sequence can also be used when a branch originates at a different angle from the main liner body 2 and/or in the case of other structural elements, such as one or more diameter changes or one or more bifurcations (again, irrespective of the angle at which these structural elements extend obliquely to the main body).

Instead of a course of the local stitch construction change 73 and/or a course of the transition to the separating threads 72 essentially perpendicular to the production direction W (horizontal) and/or essentially perpendicular to the main direction of extension 12, the local stitch construction change 73 and/or the transition to the separating threads 72 in this case preferably extends at a corresponding angle to the production direction W and/or the main direction of extension 12 (i.e. diagonally). The general sequence of basic stitch construction—local stitch construction change (for connecting the surfaces)—separating threads—basic stitch construction can be maintained, but would be successively offset in the production direction W when viewed along an axis perpendicular to the production direction W (i.e., successively formed in the production direction W at an earlier or later time).

Such a diagonal configuration of the stitch construction changes is schematically shown in FIG. 13 for a branch 30. As exemplarily shown for the lower edge region of the branch 30, the stitch construction change (basic stitch construction 70—local stitch construction change 73 for connecting the surfaces-separating threads 72—basic stitch construction 70) in the production direction W takes place in each case with a slight temporal and/or spatial delay, so that the stitch construction change is formed obliquely. As the person skilled in the art will recognize, a corresponding stitch construction sequence can take place at the upper edge region (there in reverse order). If desired, the upper and/or the lower edge region of the structural element can also be provided with a rounded course in this manner.

FIG. 14 schematically illustrates the use of such a stitch construction sequence in order to form a diameter change 10 (wherein only one half of the vascular implant 1 is shown in order to simplify the illustration). As will be apparent to the person skilled in the art, the diameter change 10 can but does not have to be formed axially symmetrically with respect to the main extension axis 2.

In order to give the diameter change 10 an oblique course, a stitch construction sequence which successively changes obliquely to the main direction of extension 12 was also chosen in this case.

In FIG. 14, a diameter reduction in the production direction W is shown, which is why the stitch construction change in the production direction W first starts at a position radially outside with respect to the main direction of extension 12 and then successively extends inwards. However, as the person skilled in the art will recognize, a diameter increase can also be produced accordingly, wherein the stitch construction change in the production direction W then first starts at a position radially inside with respect to the main direction of extension 12 and then successively extends outwards.

LIST OF REFERENCE SIGNS

1 Endovascular implant
2 Tubular main liner body
10 Diameter change
11 Length of the vascular implant
12 Main direction of extension
20 Bifurcation
21 Bifurcation length
22 Bifurcation length
23 Bifurcation angle 30 Branch
31 Branch length
32 Branch angle
40 Fenestration
50 Scallop
51 Open end
52 Recess height
53 Recess width
60 Two-needle overlap
70 Basic stitch construction
71 Edge binding
72 Separating threads
73 Local stitch construction change
80 Section with underlap
81 First section
82 Second section
83 Front textile surface
84 Back textile surface
90 Iliac vessel grafts
91 Separating threads for iliac vessel grafts
100 Method for producing an endovascular implant
110 Obtaining vessel parameters
120 Creating a computer-aided model
130 Selecting one or more structural elements
140 Determining parameters
150 Integrating the structural elements into the computer-aided model
160 Producing the vascular implant
170 Thermoforming and/or heat setting
180 Applying a stent structure
W Production direction

The invention claimed is:

1. A method for producing a vascular implant, comprising the following steps:
obtaining vessel parameters;
creating a computer-aided model of a vascular implant based on the obtained vessel parameters, wherein the vascular implant comprises one or more modules, each comprising at least one tubular liner body;
selecting one or more structural elements of a respective module from the group consisting of: one or more diameter changes along at least one tubular liner body, one or more bifurcations, one or more branches, one or more recesses, and one or more local reinforcements, wherein the one or more selected structural elements comprise one or more recesses;
determining parameters relating to the one or more selected structural elements;
integrating the structural elements into the computer-aided model according to the determined parameters;
producing the vascular implant on the basis of the created computer-aided model,
wherein the vascular implant is textile and/or textile-based, and
wherein the vascular implant is produced by warp knitting the vascular implant using a jacquard technique on the basis of the created computer-aided model; and
thermoforming and/or heat setting the vascular implant in order to expand the one or more recesses.

2. The method according to claim 1, wherein producing the vascular implant comprises integrally warp knitting the vascular implant comprising at least one module each comprising at least one tubular liner body and respective one or more structural elements.

3. The method according to claim 1, wherein the vascular implant comprises one or more bifurcations and/or one or more branches, wherein the method further comprises the steps of:
determining positions of separating threads and a corresponding local stitch construction change;
introducing the separating threads and the corresponding local stitch construction change during the production of the vascular implant; and
separating the separating threads of the produced vascular implant.

4. The method according to claim 3, wherein the vascular implant comprises one or more bifurcations and/or one or more branches, wherein the method further comprises the steps of:
determining the geometry and stitch construction change at the transition from the main liner body to the at least one bifurcation and/or at least one branch.

5. The method according to claim 3, wherein the separating threads are individual wales that are not connected to other wales by an underlap.

6. The method according to claim 1, wherein the at least one recess is a fenestration, and wherein the method further comprises the steps of:
determining positions of at least one local reinforcement at the edges of the at least one recess; and
incorporating at least one local reinforcement during the production of the vascular implant, wherein the local reinforcement comprises a change in stitch construction.

7. The method according to claim 1, wherein the vascular implant comprises one or more diameter changes along at least one tubular liner body, wherein the method further comprises the steps of:
determining parameters relating to thread tension, thread count, course density and/or stitch size.

8. The method according to claim 1, wherein the vascular implant comprises one or more diameter changes along at least one tubular liner body, wherein the method further comprises the steps of:
determining positions of separating threads and a corresponding local stitch construction change; incorporating the separating threads and the corresponding local stitch construction change during the production of the vascular implant; and separating the separating threads of the produced vascular implant.

9. The method according to claim 8, wherein the separating threads are individual wales that are not connected to other wales by an underlap.

10. The method according to claim 1, further comprising the steps of:
obtaining pre-operative medical image data of a vessel;
visualizing the obtained image data;
identifying a vessel section for which the vascular implant is to be produced; and
measuring vessel parameters.

11. The method according to claim 1, wherein the computer-aided model comprises a 3D model and/or a machine-readable file, wherein the step of producing the vascular implant is performed on the basis of the machine-readable file.

12. The method according to claim 1, further comprising application of a stent structure onto the produced vascular implant and/or of a valve at the produced vascular implant.

13. The method according to claim 12, wherein the stent structure is printed onto the vascular implant.

14. The method according to claim 1, wherein the one or more diameter changes are produced in the step of thermoforming and/or heat setting the vascular implant.

15. The method according to claim 1, wherein the angle of one or more bifurcations and/or branches relative to a main direction of extension of the vascular implant is fixed and/or modified in the step of thermoforming and/or heat setting the vascular implant.

16. The method according to claim 1, wherein the vascular implant is a stent graft.

17. The method according to claim 1, wherein the vascular implant comprises at least one first module with one or more bifurcations and at least one second module forming an iliac vessel graft.

18. The method according to claim 1, wherein the vascular implant comprises at least one recess, wherein the at least one recess is a scallop, and wherein the method further comprises the steps of:

determining positions of at least one local reinforcement at the edges of the at least one recess;

determining positions of separating threads;

incorporating at least one local reinforcement and incorporating separating threads during the production of the vascular implant, wherein the local reinforcement comprises a change in stitch construction; and separating the separating threads of the produced vascular implant.

19. The method according to claim 18, wherein the separating threads are individual wales that are not connected to other wales by an underlap, and wherein the change in stitch construction is a two needle overlap.

20. A method for producing a vascular implant, comprising the following steps:

obtaining vessel parameters;

creating a computer-aided model of a vascular implant based on the obtained vessel parameters, wherein the vascular implant comprises one or more modules, each comprising at least one tubular liner body;

selecting one or more structural elements of a respective module from the group consisting of: one or more diameter changes along at least one tubular liner body, one or more bifurcations, one or more branches, one or more recesses, and one or more local reinforcements;

determining parameters relating to the one or more selected structural elements;

integrating the structural elements into the computer-aided model according to the determined parameters;

producing the vascular implant on the basis of the created computer-aided model, wherein the vascular implant is textile and/or textile-based, and wherein the vascular implant is produced by warp knitting the vascular implant using a jacquard technique on the basis of the created computer-aided model; and placing and/or clamping the vascular implant onto a holder with a pre-stretch of at least 20% and thermoforming and/or heat setting the pre-stretched vascular implant.

21. A method for producing a vascular implant, comprising the following steps:

obtaining vessel parameters;

creating a computer-aided model of a vascular implant based on the obtained vessel parameters, wherein the vascular implant comprises one or more modules, each comprising at least one tubular liner body;

selecting one or more structural elements of a respective module from the group consisting of: one or more diameter changes along at least one tubular liner body, one or more bifurcations, one or more branches, one or more recesses, and one or more local reinforcements, wherein the one or more selected structural elements comprise one or more recesses, and wherein the at least one recess is a fenestration;

determining parameters relating to the one or more selected structural elements;

integrating the structural elements into the computer-aided model according to the determined parameters;

producing the vascular implant on the basis of the created computer-aided model, wherein the vascular implant is textile and/or textile-based, and wherein the vascular implant is produced by warp knitting the vascular implant using a jacquard technique on the basis of the created computer-aided model;

determining positions of at least one local reinforcement at the edges of the at least one recess; and incorporating at least one local reinforcement during the production of the vascular implant, wherein the local reinforcement comprises a change in stitch construction.

* * * * *